(12) United States Patent
Horiuchi et al.

(10) Patent No.: US 8,398,936 B2
(45) Date of Patent: Mar. 19, 2013

(54) CAPILLARY PUMP UNIT AND FLOW CELL

(75) Inventors: Tsutomu Horiuchi, Tokyo (JP); Toru Miura, Tokyo (JP); Yuzuru Iwasaki, Tokyo (JP); Michiko Seyama, Tokyo (JP); Tsuyoshi Hayashi, Tokyo (JP); Jun-ichi Takahashi, Tokyo (JP); Tsuneyuki Haga, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 75 days.

(21) Appl. No.: 12/811,162

(22) PCT Filed: Jan. 7, 2009

(86) PCT No.: PCT/JP2009/050087
§ 371 (c)(1),
(2), (4) Date: Jun. 29, 2010

(87) PCT Pub. No.: WO2009/088021
PCT Pub. Date: Jul. 16, 2009

(65) Prior Publication Data
US 2010/0303686 A1    Dec. 2, 2010

(30) Foreign Application Priority Data

Jan. 8, 2008 (JP) ................................ 2008-001064
Sep. 25, 2008 (JP) ................................ 2008-246604

(51) Int. Cl.
*G01N 33/48* (2006.01)
*F15C 1/06* (2006.01)

(52) U.S. Cl. ...................................................... 422/504

(58) Field of Classification Search .................. 422/412, 422/504, 507
See application file for complete search history.

(56) References Cited

U.S. PATENT DOCUMENTS

| 4,960,691 | A | 10/1990 | Gordon et al. |
| 5,500,071 | A | 3/1996 | Kaltenbach et al. |
| 6,964,871 | B2 * | 11/2005 | Bell et al. ........................ 436/95 |
| 2002/0086436 | A1 | 7/2002 | Buechler |
| 2002/0179448 | A1 | 12/2002 | Lauks |
| 2003/0127333 | A1 | 7/2003 | Lauks et al. |

(Continued)

FOREIGN PATENT DOCUMENTS

| JP | H07-036017 | 2/1995 |
| JP | 07-036017 B2 | 4/1995 |

(Continued)

OTHER PUBLICATIONS

Yuzuru Iwasaki, Osamu Niwa, "Koso—Kotai Fukugo Hanno System o Riyo suru Micro Ryuro Intelligent Sensor", Dai 13 Kai Intelligent Zairyo / System Symposium Koen Yoshishu, Mar. 8, 2004, Dai 13 Kai, pp. 34 to 35.

(Continued)

*Primary Examiner* — In Suk Bullock
*Assistant Examiner* — Timothy G Kingan
(74) *Attorney, Agent, or Firm* — Harness, Dickey & Pierce, P.L.C.

(57) ABSTRACT

In a capillary pump unit, a capillary pump including a plurality of through portions making a first point and a second point of an approximately flat-plate-shaped base communicable with each other are formed in the base, and a sample liquid is transferred from the first point to the second point by capillary force by the through portions.

5 Claims, 18 Drawing Sheets

U.S. PATENT DOCUMENTS

| | | | |
|---|---|---|---|
| 2005/0287044 A1* | 12/2005 | Natarajan | 422/102 |
| 2006/0043284 A1 | 3/2006 | Baba et al. | |
| 2006/0263914 A1 | 11/2006 | Sando et al. | |

FOREIGN PATENT DOCUMENTS

| | | |
|---|---|---|
| JP | 08-334505 A | 12/1996 |
| JP | 2000-329766 A | 11/2000 |
| JP | 2001-194298 A | 7/2001 |
| JP | 2002-214131 A | 7/2002 |
| JP | 2004-053372 A | 2/2004 |
| JP | 2004-219325 A | 8/2004 |
| JP | 2005-279523 A | 10/2005 |
| JP | 2005-297150 A | 10/2005 |
| JP | 2005-300038 A | 10/2005 |
| JP | 2005-532151 A | 10/2005 |
| JP | 2006-508350 A | 3/2006 |
| JP | 2006-334741 A | 12/2006 |
| JP | 2007-196219 A | 8/2007 |
| WO | WO-03/103835 A1 | 12/2003 |
| WO | 2005/075975 A1 | 8/2005 |
| WO | WO-2006/123578 A1 | 11/2006 |
| WO | WO-2007/013287 A1 | 2/2007 |
| WO | WO-2008/001737 A1 | 1/2008 |

OTHER PUBLICATIONS

Tsutomu Horiuchi et al., "Gaibu Pump Fuyo na SPR Sokutei o Kano ni suru Shuseki Mosaikan Passive Flow Chip no Kaihatsu", Dai 55 Kai Extended Abstracts, Japan Society of Applied Physics and Related Societies, Mar. 27, 2008, separate vol. 3, p. 1353, 27a-R-4.

Martin Zimmermann et al., "Capillary pumpus for autonomous capillary systems", The Royal Society of Chemistry, Lab on a Chip, vol. 7, pp. 119-125, 2007.

Joo-Eun Kim et al., "Functional Membrane-Implanted Lab-on-a-Chip for Analysis of Percent HDL Cholesterol", Analytical Chemistry, vol. 77, No. 24, Dec. 15, 2005, pp. 7901-7907.

* cited by examiner

CAPILLARY PUMP UNIT AND FLOW CELL

TECHNICAL FIELD

The present invention relates to a capillary pump unit which suctions a sample liquid as a target using a capillary force, and a flow cell including the capillary pump unit.

The present application claims priority on Japanese Patent Applications No. 2008-001064 filed on Jan. 8, 2008 and No. 2008-246604 filed on Sep. 25, 2008, the entire contents of which are incorporated herein by reference.

BACKGROUND ART

Measurement using an enhanced biomolecular identification function such as coupling of antigen-antibody reaction or DNA fragment (DNA probe) and DNA is an important technique for measurement in the field of laboratory testing and biochemistry and measurement of environmental pollution substances.

Examples include micro total analysis systems (TASs), micro combinatorial chemistry, chemical IC, chemical sensors, bio sensors, micro analysis, electrochemistry analysis, QCM measurement, SPR measurement, ATR measurement, and so on, but in such measurement fields, a small amount of a sample liquid is mostly used.

As a method of measuring a chemical substance in a sample liquid, an optical measurement method in which a molecule selective substance is fixed in advance, the sample liquid is caused to flow through the molecule selective substance, and coupled molecules are selectively detected, is known. As a type of the optical measurement method, there is a method using a total reflection optical system. In this method, coupling near a surface can be measured directly and with high sensitivity using an excited evanescent wave as a probe light.

In the total reflection optical system, a surface plasmon resonance (SPR) measurement method using the fact that an evanescent wave excited by total reflection resonates with surface plasmon of a surface of a thin metallic film formed on a substrate surface and absorbed is particularly widely used.

When a sample liquid is measured using the surface plasmon resonance measurement method, a groove is formed on a substrate to provide a micro flow channel, probe molecules are fixed on a metal film disposed in the flow channel, and the sample liquid is caused to pass through the flow channel. Based on interaction between the probe molecules and target substance in the sample liquid at this time, measurement is performed to determine whether the target substance is contained in the sample liquid (see, for example, Patent Document 1 or 2).

Also, as a method of analyzing a small amount of a sample liquid, an analysis method using paper chromatography is known. For example, as simple inexpensive means for biological substance measurement, an enhanced immunochromatography method, an immuneconcentration method, and so on, have been proposed (see, for example, Patent Document 3 or 4). Even in these methods, a sample liquid is required to pass through a micro flow channel on a substrate.

In the above-described measurements and analyses, a small amount of a sample liquid is transferred to a detector so that a higher sensitivity and efficiency measurement can be performed without causing a reduction in the concentration of the sample liquid. As techniques for realizing transfer of a small amount of a solution, there are a method of forming a flow channel having a width of hundreds of μm on a substrate and transferring a solution under external pressure, a method of transferring a solution using electrostatic force, an electrowetting method, a method of transferring a solution using a volume change or air bubble generation caused by heating, a method using electro-osmotic flow, and so on.

However, in order to transfer a small amount of a sample liquid using such methods, a flow channel needs to be formed on a substrate and other components need to be provided on the same substrate. Accordingly, it is difficult to fabricate such a device. Also, for example, where the sample liquid is transferred under external pressure, separate parts such as a pump or a tube are necessary in addition to the substrate constituting the flow channel. As a result, a transfer path, such as a tube, makes dead volume of the sample liquid, which limits use to a small amount of the sample liquid.

Accordingly, a method of forming a region of a flow channel or a pump that transfers a sample liquid using a capillary force between opposing surfaces of two substrates using a micro machining technique has been proposed (see, for example, Patent Document 5 and Non-Patent Document 1 or 2). A measuring chip (flow cell) fabricated using this technique includes an inlet through which a sample liquid is introduced, and a pump which suctions the sample liquid using capillary force. When the sample liquid is introduced to the inlet, the sample liquid flows sequentially from the inlet to a measurement flow channel and the pump, and when the sample liquid reaches the capillary pump, the sample liquid is suctioned due to a capillary force occurring in the pump. Accordingly, the sample liquid introduced in the inlet flows through the measurement flow channel due to a suction capillary force of the pump.

However, in the flow cell as described above, since a change due to binding reaction of probe molecules fixed to the metal film and target substance and a change due to a foreign substance precipitated and sedimented on the probe molecules are not discriminated, it is necessary to continuously flow the sample fluid in the measurement flow channel by suppressing precipitation of the foreign substance and improving measurement precision.

Also, it is necessary to flow the sample fluid in the measurement flow channel by a time required to detect the target substance and necessary to flow a greater amount of the sample fluid when the concentration of the target substance is decreased.

According to the requirements, the capacity of the pump can be increased for a greater amount of flowing sample fluid. However, in this case, it is effective to form a measuring chip that is large in a height direction to obtain a structure having a high aspect ratio, thereby reserving a volume of the pump in a height direction inside the measuring chip.

Meanwhile, in order to obtain a small measuring chip, it is necessary to improve efficiency of space use of the flow channel or the pump in the measuring chip. Accordingly, it is desirable to form components, such as a flow channel or a pump, in all regions inside the measuring chip in the height direction.

However, in techniques of Patent Document 5 and Non-Patent Document 2, since a flow channel formed on a substrate has an additional function to serve as a capillary pump, the capacity of the capillary pump is necessarily limited to a height range of the flow channel.

That is, a height of the capillary pump ranges from about 10 μm to about 100 μm as described in Patent Document 5 and is 30 μm as described in Non-Patent Document 2. Such a limit is caused by providing an additional function to the capillary pump, which has a unique function of flowing the sample liquid.

Accordingly, in order to sufficiently reserve the capacity of the pump, it is necessary to extend the measuring chip in a plane direction, which makes it difficult to fabricate the measuring chip with a small size and at a low cost.

Meanwhile, since lithography or etching is performed on a substrate formed of a material or a substrate itself having a groove as a flow channel is fabricated by injection molding to fabricate the measuring chip, it is difficult to fabricate a structure of a high aspect ratio. Accordingly, since the capacity of the pump is limited, the amount of the sample liquid flowing through the measurement flow channel is also limited and the sample liquid cannot be continuously flowed for sufficient measurement.

Also, in the fabricating method, because it is difficult to process the inside of the substrate, locations in the substrate at which a flow channel or a pump can be fabricated are limited, making it impossible to fabricate a structure with a high efficient use of space.

Patent Document 1: Japanese Patent Application, First Publication No. 2001-194298

Patent Document 2: Japanese Patent Application, First Publication No. 2002-214131

Patent Document 3: Japanese Patent Application, Second Publication No. H7-036017

Patent Document 4: Japanese Patent Application, First Publication No. 2000-329766

Patent Document 5: Patent Application Publication No. 2005-532151

Non-Patent Document 1: Amal. Chem. 2005, 77, 7901-7907.

Non-Patent Document 2: M. Zimmermann, et al., "Capillary pumps for autonomous capillary systems," The Royal Society of Chemistry, Lob on a Chip, Vol. 7, pp. 119-125, 2007.

DISCLOSURE OF INVENTION

Problem to be Solved by the Invention

This invention has been achieved in view of such problems, and it is an object of the present invention to provide a capillary pump unit and a flow cell that can have high pump capacity and can be fabricated with a small size at a low cost.

It is another object of the present invention to provide a capillary pump unit which suctions a sample liquid up that has a high aspect ratio, a high pump capacity, and a highly efficient use of space, and a flow cell using the capillary pump unit.

Means for Solving the Problem

In order to achieve the objects, the present invention proposes the following means.

That is, in the capillary pump unit according to the present invention, there is an approximately flat-plate-shaped base, a capillary pump comprising a plurality of through portions making a first point and a second point of the approximately flat-plate-shaped base communicable with each other, the capillary pump being formed in the approximately flat-plate-shaped base, and an inlet formed in the approximately flat-plate-shaped base, wherein the inlet distributes sample liquid to the plurality of through portions, and the sample liquid is transferred from the first point to the second point by capillary force by the plurality of through portions.

According to the capillary pump unit, since the capillary pump which transfers the sample liquid using a capillary force can be provided separately from the flow channel through which the sample liquid passes, the pump capacity can be increased in a height direction without being limited by the height of the flow channel, i.e., a vertical interval. Accordingly, sufficient pump capacity can be reserved without increasing the area in a plane direction.

Also, in the capillary pump unit according to the present invention, the base may include a plurality of stacked sheet-shaped bases, and a plurality of through portions may be formed in the respective sheet-shaped bases so that the sheet-shaped bases are communicable with one another.

According to the capillary pump unit, since the capillary pump unit is formed by stacking a plurality of sheet-shaped bases, the volume can be increased in a height direction by properly increasing the number of the stacked sheet-shaped bases. Thus, a capillary pump having a structure of a high aspect ratio can be readily formed.

Also, since the through portions formed in the respective sheet-shaped bases are communicable with one another among the sheet-shaped bases, very small spaces in which a capillary force occurs can be formed in all regions of the stacked sheet-shaped bases in a vertical direction, thus reserving a highly efficient use of space.

Also, in the capillary pump unit according to the present invention, preferably, the sheet-shaped base may be a seal to which both sides or a single side can be adhered, and the plurality of the seals may be adhered to one another and stacked. Also, in the capillary pump according to the present invention, preferably, the sheet-shaped base may be formed of synthetic resin or glass, and a plurality of synthetic resin or glass may be welded to one another and stacked.

Thus, the sheet-shaped bases can be readily stacked to form a capillary pump.

Also, in the capillary pump unit according to the present invention, the through portions may be a plurality of through holes formed in the respective sheet-shaped bases, and the sheet-shaped bases may be stacked so that at least some of the through holes of the adjacent ones of the sheet-shaped bases overlap each other.

According to the capillary pump unit, a liquid can be readily suctioned by capillary force by the cylindrical hollow portions in which the through holes overlap one another.

Also, in the capillary pump unit according to the present invention, the through portions may be a plurality of through grooves provided in parallel with one another in the respective sheet-shaped bases, and the sheet-shaped bases may be stacked so that the through grooves of adjacent ones of the sheet-shaped bases overlap in parallel with one another.

According to the capillary pump unit, a liquid can be readily suctioned by capillary force by the slit-shaped hollow portions in which the through holes overlap one another.

Also, in the capillary pump unit according to the present invention, the through portions may be a plurality of through grooves provided in parallel with one another in the respective sheet-shaped bases, and the sheet-shaped bases may be stacked so that the through grooves of adjacent ones of the sheet-shaped bases intersect and overlap each other.

With this capillary pump, since the plurality of through grooves formed in the sheet-shaped bases intersect each other between the vertically contiguous sheet-shaped bases, all the through grooves are communicable with one another and the hollow portions are formed in a parallel-cross shape. In the hollow portions in a parallel-cross shape, a large contact area between the sample liquid and the sheet-shaped base increases the capillary force so that the liquid can be efficiently suctioned.

Effect of the Invention

With the capillary pump unit according to the present invention, sufficient pump capacity can be reserved without increasing the area in a plane direction, thus obtaining high pump capacity and achieving a small size and low cost. In addition, a structure having a high aspect ratio can be readily made by stacking the sheet-shaped bases, thus obtaining high pump capacity. Also, the through portions of the respective sheet-shaped bases are communicable with one another, thus realizing a highly efficient use of space.

Furthermore, with the flow cell according to the present invention, a sample liquid can be continuously flowed by employing the capillary pump unit, such that measurement by the detector can be successfully performed and high reliability of the measurement result can be obtained.

REFERENCE SYMBOLS

10 . . . flow cell, 11 . . . substrate, 12 . . . capillary pump unit, 13 . . . inlet, 13a . . . inlet (first portion), 13b . . . communication portion (second portion), 14 . . . capillary pump, 15 . . . measurement flow channel, 16 . . . detector, 18 . . . cylindrical hole (through portion), 19 . . . suction flow channel, 24 . . . sheet-shaped base, 24a . . . sheet-shaped base, 24b . . . sheet-shaped base, 27 . . . through hole, 30 . . . flow cell, 32 . . . suction flow channel, 40 . . . flow cell, 44 . . . suction flow channel, 45 . . . surface active region, 50 . . . flow cell, 51 . . . substrate, 52 . . . capillary pump unit, 53 . . . inlet, 54 . . . capillary pump, 55 . . . measurement flow channel, 56 . . . detector, 57 . . . suction flow channel, 62 . . . through groove, 70 . . . sheet-shaped base, 70a . . . sheet-shaped base, 70b . . . sheet-shaped base, 70c . . . sheet-shaped base, 80 . . . flow cell, 81 . . . capillary pump, 82 . . . through groove, 90 . . . sheet-shaped base, 90a . . . sheet-shaped base, 90b . . . sheet-shaped base, 90c . . . sheet-shaped base, 90d . . . sheet-shaped base, 90e . . . sheet-shaped base

BEST MODE FOR CARRYING OUT THE INVENTION

Hereinafter, a first embodiment of the present invention will be described with reference to the accompanying drawings.

Figure 1:
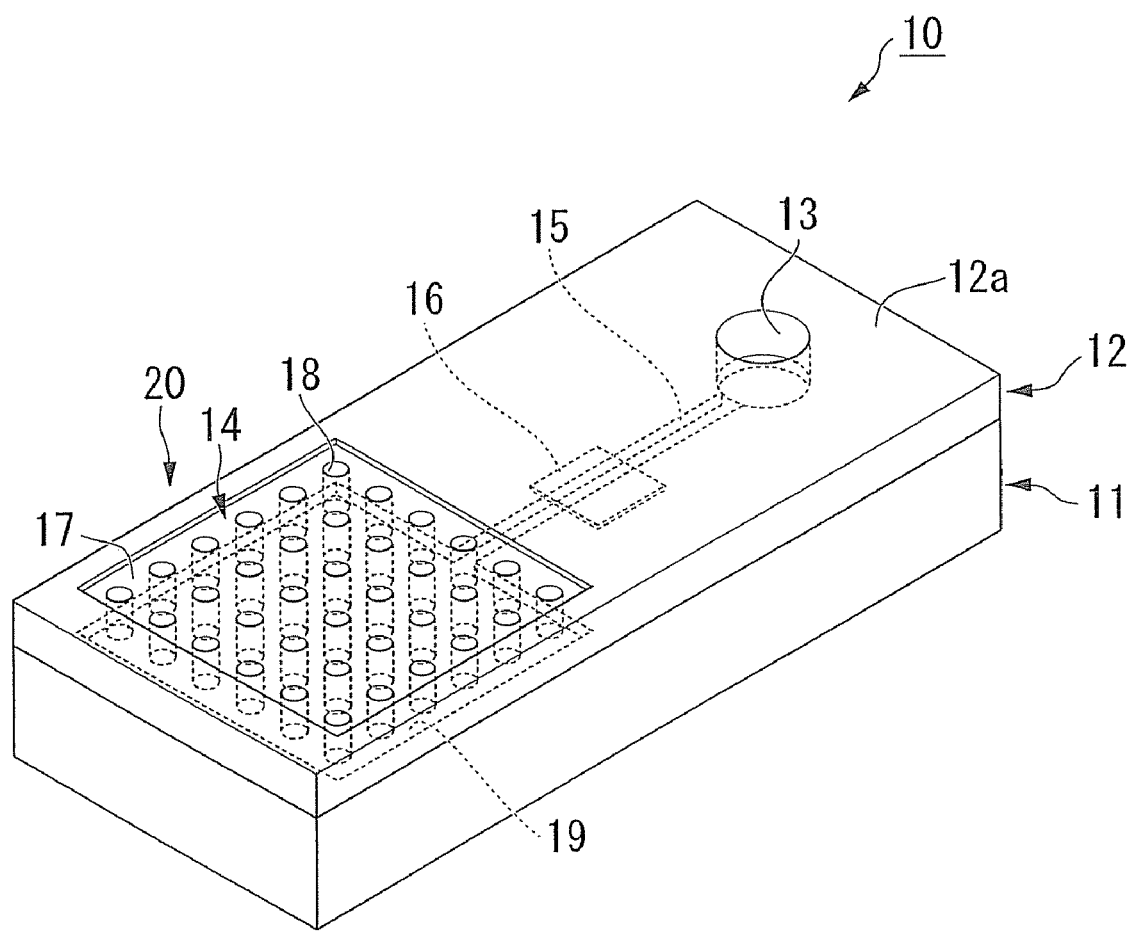
FIG. 1 is a perspective view of a flow cell according to a first embodiment.
Figure 2:
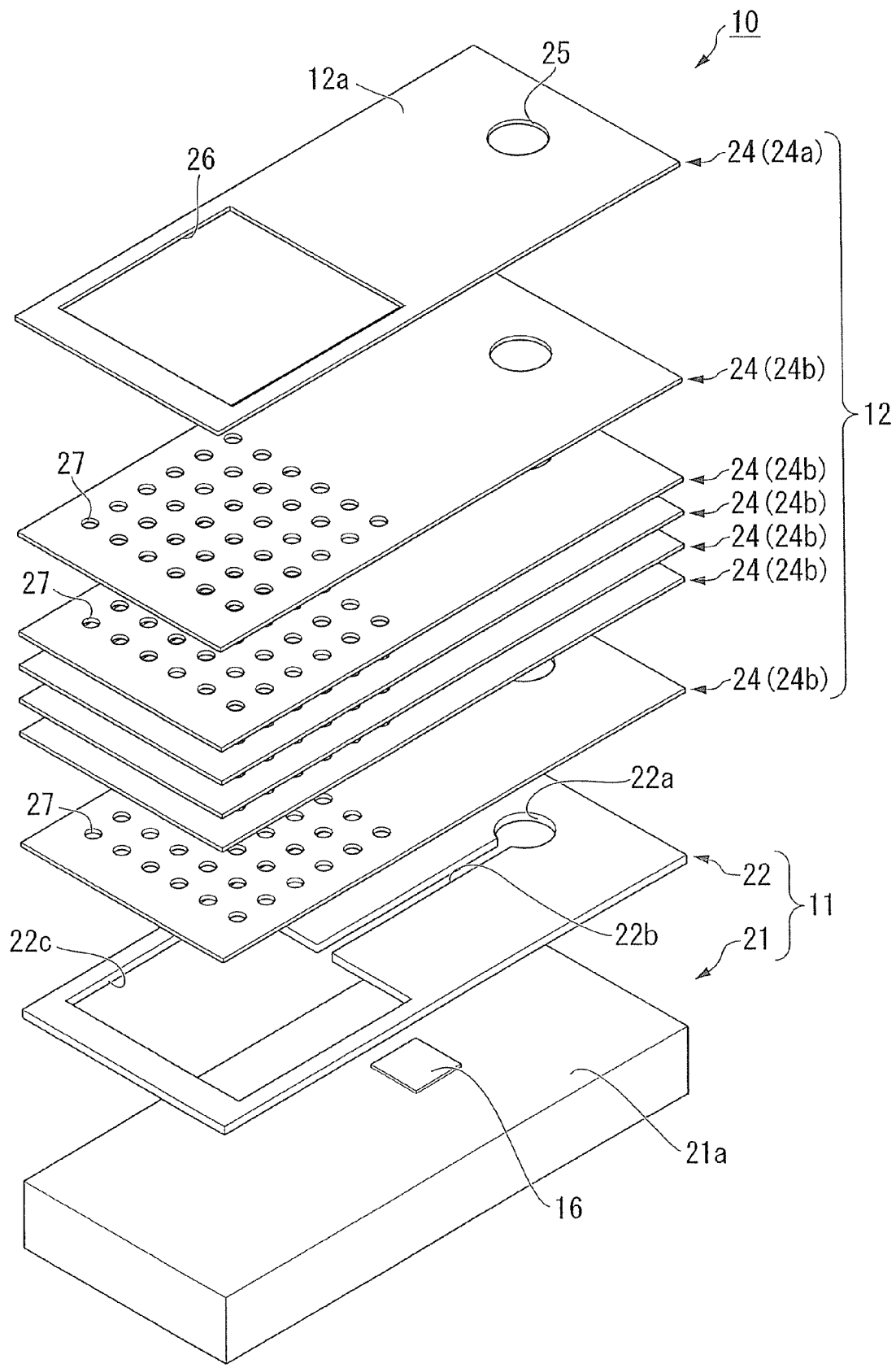
FIG. 2 is an exploded perspective view of the flow cell according to the first embodiment.

FIG. 1 is a perspective view of a flow cell according to the first embodiment, and FIG. 2 is an exploded perspective view of the flow cell according to the first embodiment.

As shown in FIG. 1, a flow cell 10 of the present embodiment is formed by stacking a flat-plate-shaped capillary pump unit 12 disposed with the same outside dimension as an approximately flat-plate-shaped substrate 11 that is in a rectangular shape when viewed from above, on the substrate 11.

An inlet 13 through which a sample liquid (referred to as a sample) is introduced, a capillary pump 14 which suctions the sample liquid up, a suction flow channel 19 disposed beneath the capillary pump 14, a measurement flow channel 15 that connects between the suction flow channel 19 and the inlet 13, a detector 16 provided on the measurement flow channel 15, and an outlet portion 17 disposed on the capillary pump 14 of the capillary pump unit 12 are provided in the flow cell 10, as shown in FIG. 1.

Furthermore, the outlet portion 17 need not necessarily be provided.

The substrate 11 is formed by disposing a spacer portion 22 on an upper surface 21a of a base substrate 21, as shown in FIG. 2. The base substrate 21 is formed of, for example, optical glass, such as BK7, or a polymer material in a plate shape having a constant thickness. Meanwhile, the spacer portion 22 is formed of, for example, a resin film to a smaller thickness than the base substrate 21.

In the rectangular spacer portion 22, a circular hole 22a is formed in a region beside one short side in a longitudinal direction and in a region of an approximately central portion of the short side in a width direction, and a flow channel groove 22b having a first end connected to the circular hole 22a and extending toward the other short side of the spacer portion 22 is formed. A rectangular hole 22c connected to a second end of the flow channel groove 22b and having an outline formed along an outline of the spacer portion 22 is formed in a portion beside a second side of the spacer portion 22.

And, in the present embodiment, the capillary pump unit 12 is formed by stacking a plurality of sheet-shaped bases 24 in a thickness direction of the capillary pump unit 12. Alternatively, the capillary pump unit 12 may be formed of one sheet-shaped base 24, instead of stacking the plurality of the sheet-shaped bases 24.

The sheet-shaped base 24 in a rectangular shape, when viewed from above, having the same peripheral size as the substrate 11 is formed as a thin film having a thickness of 10 μm to 100 μm. Also, in the present embodiment, the sheet-shaped base 24 is formed in a double-sided tape form, both sides of which are coated with adhesive. Specifically, the TL-4005 series available from Lintec Corporation, a general-purpose double-sided tape 9313 available from Sumitomo 3M Limited, ARcare series available from NIPPN Techno-Cluster, Inc., or the like is used.

Further, the sheet-shaped base 24 is not limited to the double-sided tape form, but may be formed of acryl or glass in a thin film form or of a metallic sheet or a ceramic sheet. Also, the thickness is not limited to the above range, but may range, for example, from 100 μm to several mm.

In the rectangular sheet-shaped base 24, a circular hole 25 having the same diameter as the circular hole 22a of the spacer portion 22 is formed in a region beside one short side in a longitudinal direction and in a region of an approximately central portion of the short side in a width direction.

Also, in the sheet-shaped base 24a that is a top layer of the plurality of sheet-shaped bases 24, a rectangular hole 26 having the same size as the rectangular hole 22c of the spacer portion 22 is formed in a portion of the sheet-shaped base 24a corresponding to the rectangular hole 22c.

Meanwhile, a plurality of through holes 27 (also referred to as through portions) are formed and arranged in a lattice shape in portions of the sheet-shaped bases 24b, excluding the sheet-shaped base 24a as a top layer, corresponding to the rectangular holes 22c and 26.

As the sheet-shaped bases 24 are stacked to form the capillary pump unit 12, an outlet portion 17 is formed by the rectangular hole 26 of the sheet-shaped base 24a as a top layer on an upper surface 12a of the capillary pump unit 12, as shown in FIG. 1, and as the through holes 26 of the respective sheet-shaped bases 24b are communicable with one another, a plurality of cylindrical holes (through portions) 18 are formed inside the capillary pump unit 12.

Also, the sheet-shaped base 24 as a top layer need not necessarily be formed, and in this case, the outlet portion 17 is not formed.

Here, a diameter of the cylindrical hole 18, i.e., a diameter of the through hole 27 of the sheet-shaped base 24 has such a size that a capillary force occurs for a sample liquid. Accordingly, the plurality of cylindrical holes 18 function as the capillary pump 14 which suctions the sample liquid due to a capillary force.

Further, the flow cell 10 of the present embodiment is not limited to the configuration in which the capillary pump unit 12 is formed by stacking the sheet-shaped bases 24 as described above, but, for example, the capillary pump unit 12 may be formed by performing a laser machining, and so on, on a single plate-shaped member having a constant thickness to form the through holes 27 or the inlet 13.

And, the capillary pump unit 12 is provided on the substrate 11 to obtain the flow cell 10 of the present embodiment.

At this time, the circular hole 25 of each sheet-shaped base 24 and the circular hole 22a of the spacer portion 22 in the substrate 11 overlap each other to form the inlet 13 through which the sample liquid is introduced.

Also, an upper portion of the flow channel groove 22b of the spacer portion 22 is blocked by a lower surface 12b of the capillary pump unit 12 to form a measurement flow channel 15 through which the sample liquid introduced to the inlet 13 is flowed, and a detector 16 is disposed on the measurement flow channel 15.

Similarly, an upper portion of the rectangular hole 22c of the spacer portion 22 is blocked by the lower surface 12b of the capillary pump unit 12 to form a suction flow channel 19 through which the sample liquid is suctioned by the capillary pump 14.

A vertical interval between the measurement flow channel 15 and the suction flow channel 19, i.e., a thickness of the spacer portion 22, has such a size that a capillary force occurs for the sample liquid. Accordingly, the sample liquid introduced to the inlet 13 flows through the inside of the measurement flow channel 15 and the suction flow channel 19 due to the capillary force.

The flow cell 10 of the present embodiment is formed by stacking the substrate 11 and the plurality of sheet-shaped bases 24, as described above. However, where the sheet-shaped bases 24 have at least a first side that is an adhesive side, the plurality of sheet-shaped bases 24 are sequentially disposed on an upper surface of the substrate 11 to be adhered to each other, thus obtaining a flow cell 10 in which the substrate 11 and the respective sheet-shaped bases 24 are integrally fixed.

Alternatively, where the sheet-shaped bases 24 are formed of acryl or glass, or of a metallic sheet, a ceramic sheet, or the like, the sheet-shaped bases 24 are integrally stacked using adhesive, the plurality of sheet-shaped bases 24 are sequentially disposed on the upper surface of the capillary pump unit 12 and then heated or irradiated with laser light to be welded, or the substrate 11 and the respective sheet-shaped bases 24 are integrally fixed using anodic bonding to form the flow cell 10.

Figure 3:
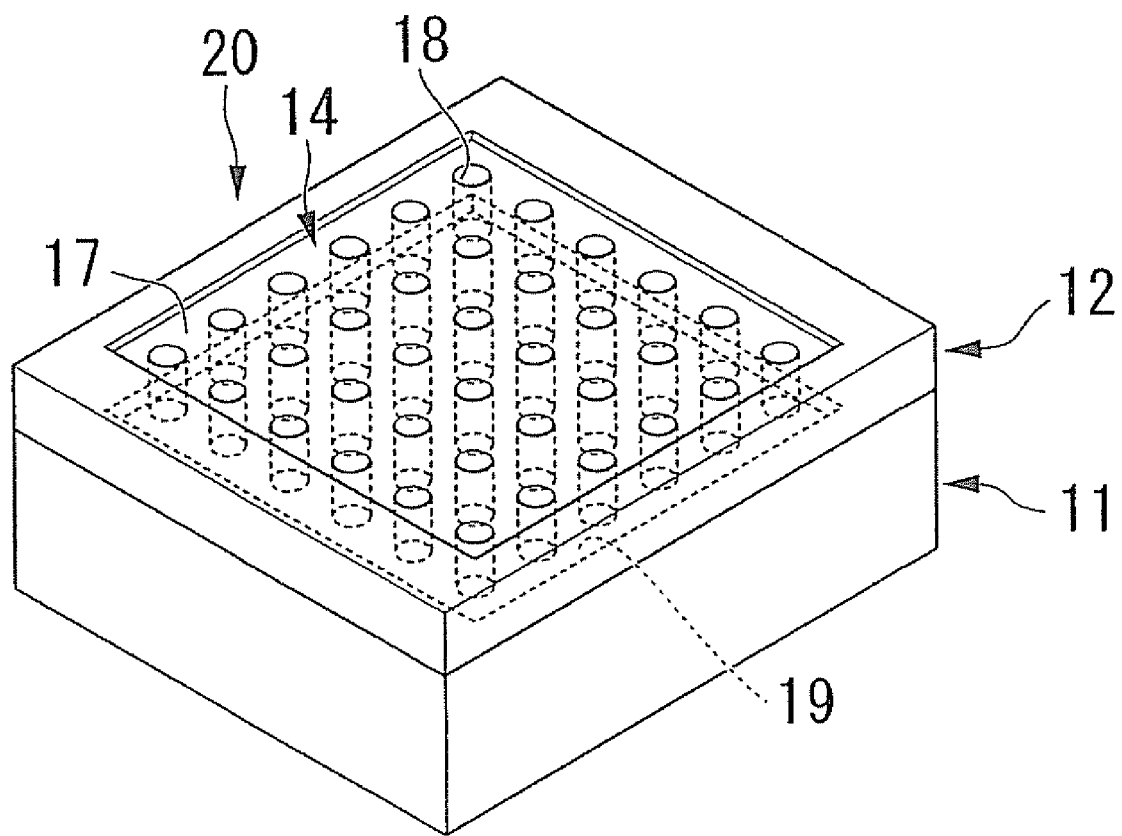
FIG. 3 is a plan view of a capillary pump unit according to the first embodiment.
Figure 4:
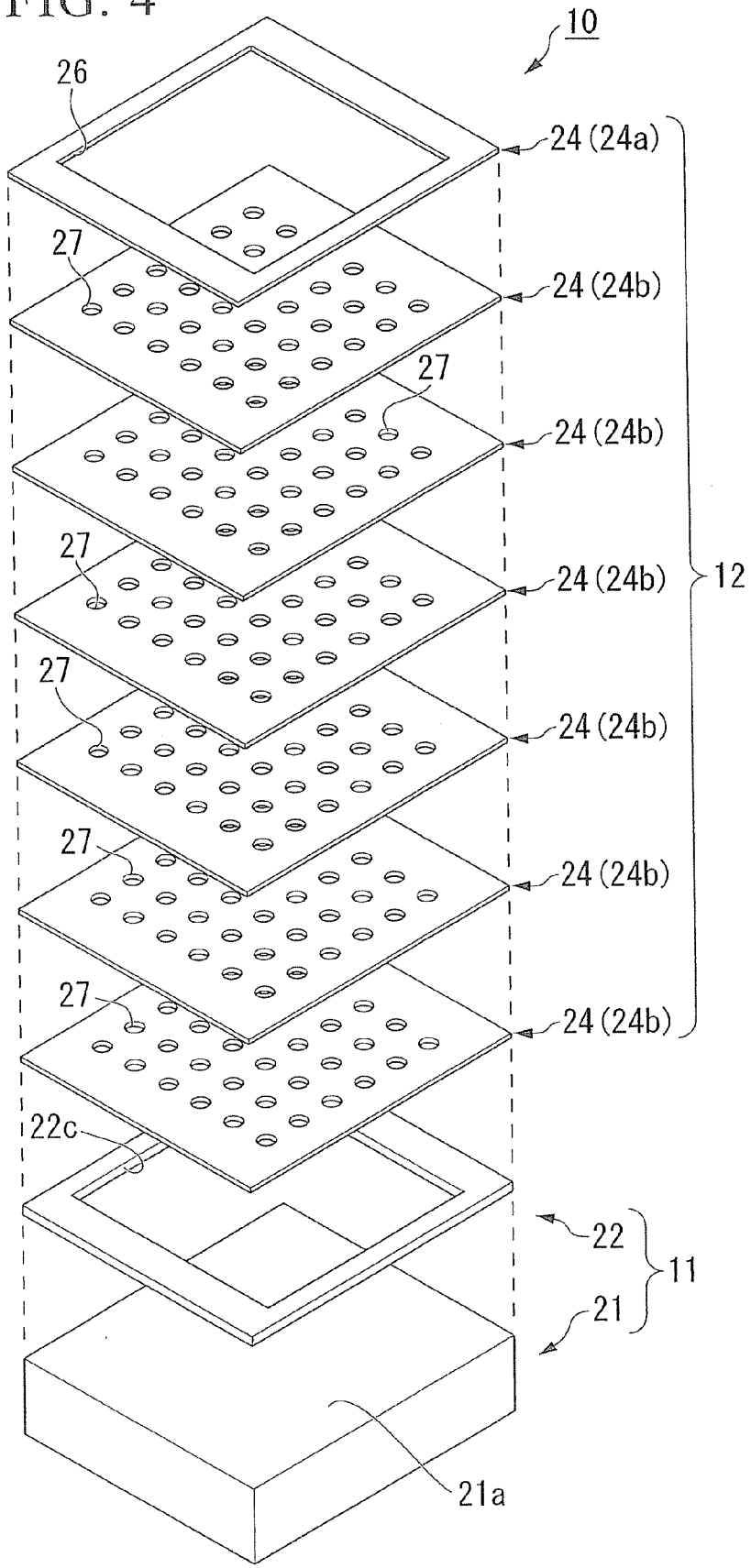
FIG. 4 is an exploded perspective view of the capillary pump unit according to the first embodiment.

Further, for example, the flow cell 10 may not include the inlet 13, the measurement flow channel 15 and the detector 16, as shown in FIGS. 3 and 4. Even in this case, sample liquid introduced to the suction flow channel 19 via another flow channel (not shown) is transferred upward by the capillary pump 14 including a plurality of cylindrical holes 18.

Next, an operation of the flow cell 10 according to the present embodiment will be described.

When a sample liquid is injected into the inlet 13, the sample liquid flows into the measurement flow channel 15 due to the capillary force. When the sample liquid passes through the detector 16 on the measurement flow channel 15, measurement using a surface plasmon resonance phenomenon is performed.

The measurement using a surface plasmon resonance phenomenon uses resonance of an evanescent wave and a surface plasmon wave on a surface of metal (in the present embodiment, the thin metallic film) with which the sample liquid is brought into contact.

Figure 20:
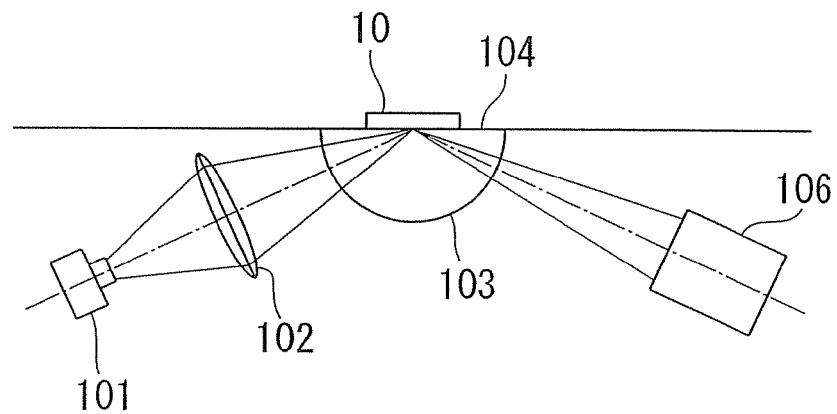
FIG. 20 is a diagram showing an example of a configuration of an SPR measurement apparatus.
Figure 21:
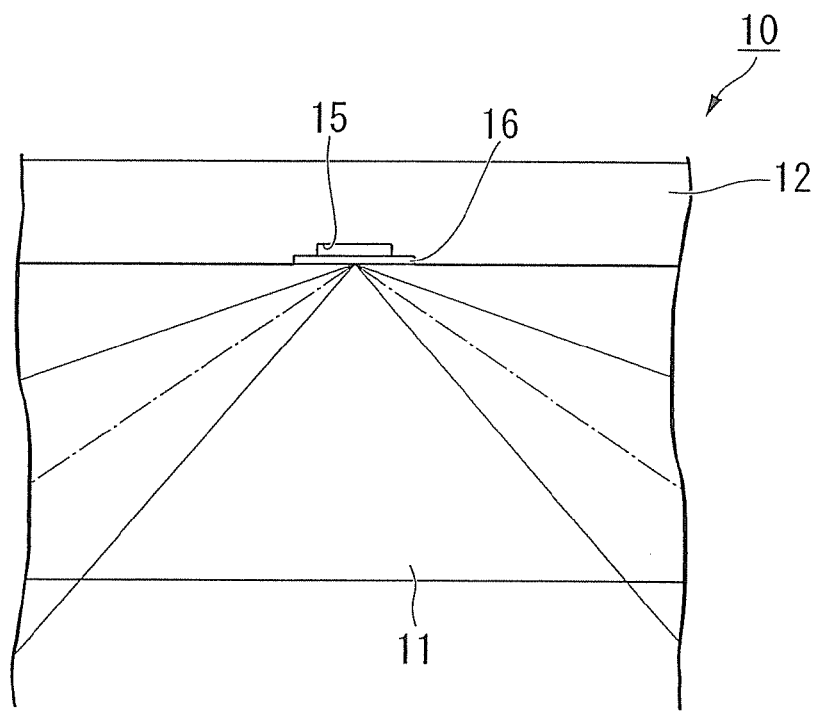
FIG. 21 is a partially enlarged view of the SPR measurement apparatus shown in FIG. 20.

In this measurement, as shown in FIGS. 20 and 21, light output from a light source 101 is concentrated by an incident-side lens 102, input to a prism 103, and irradiated to the detector 16, which functions as a measuring unit for the flow cell 10 closely adhered to an upper surface 104 of the prism 103. A sample liquid used as a sample is brought into contact with the surface of the detector 16, and at this time, a rear surface of the detector 16 is irradiated with light transmitting through the substrate 11.

The irradiated light is reflected from an interface between the substrate 11 and the detector 16, and the intensity of the light is measured by a light detector 106, which includes an imaging device, such as a CCD image sensor. A valley at which reflectivity is reduced at an angle at which the resonance occurs is observed.

In the measurement, it is detected whether there is a sample that is selectively bind to an antibody or DNA fragment fixed to the surface of the detector 16. However, when the sample liquid is at rest on the detector 16, a change due to binding reaction of target substance (antigen) and the antibody and a change due to foreign substance precipitated and sedimented on the detector are not discriminated. On the other hand, the sample liquid is flowed at the detector 16 so that the precipitation of the foreign substance is suppressed, and the above-described change due to the binding reaction is selectively detected, such that the measurement can be accurately performed. That is, the sample liquid continuously flows through the measurement flow channel 15, such that high-precision measurement can be performed.

The sample liquid passing through the measurement flow channel 15 reaches the suction flow channel 19. The sample liquid flows into and fills the capillary pump 14 due to the capillary force of the capillary pump 14 including the plurality of cylindrical holes 18. Accordingly, the sample liquid injected into the inlet 13 flows through the measurement flow channel at a predetermined flow rate and the measurement is performed. When the sample liquid reaches the outlet portion 17 located on the capillary pump 14, the sample liquid stops movement. Accordingly, the sample liquid suction operation in the capillary pump 14 is terminated.

Thus, according to the flow cell 10 in the present embodiment, the capillary pump 14 in which the plurality of cylindrical holes 18 are provided functions as a transfer portion for causing the sample liquid introduced through the inlet 13 to flow through the measurement flow channel 15 at a predetermined flow rate (flow volume).

Here, in order to successfully measure the sample liquid, it is necessary to continuously flow the sample liquid in the measurement flow channel 15, and it is desirable to increase capacity of the capillary pump 14 for accommodating the sample liquid.

In this regard, in the flow cell 10 according to the present embodiment, since the capillary pump 14 is provided separately from the measurement flow channel 15 and the suction flow channel 19, the pump capacity can be increased in a height direction without being limited by the heights of the measurement flow channel 15 and the suction flow channel 19. Accordingly, sufficient pump capacity can be reserved without increasing the area in a plane direction.

Further, in the flow cell 10 according to the present embodiment, since the capillary pump 14 is formed by stacking the plurality of sheet-shaped bases 24, the size of the flow cell 10 can increase in a height direction only by increasing the number of the sheet-shaped bases 24. Accordingly, the capillary pump 14 having a structure of a high aspect ratio can be readily formed.

Thus, since a large volume of the capillary pump 14 can be reserved in a stacking direction, the capacity for accommodating the sample liquid can be increased and the sample liquid can be continuously flowed by the measurement flow channel 15. Accordingly, sufficient measurement of the sample liquid can be performed for improved measurement precision.

Further, since the through holes 27 formed in the respective stacked sheet-shaped bases 24 are communicable with one another to form the cylindrical holes 18 of the capillary pump 14, very small spaces in which a capillary force occurs can be formed in all regions of the stacked sheet-shaped bases 24 in a vertical direction, such that a highly efficient use of space in the flow cell 10 can be reserved.

Here, the cylindrical holes 18 will be discussed. First, as well known, an elevation height h (in m) of liquid surface in the capillary is given as "$h=(2\gamma \cos\theta)/(\rho g r)$". Here, $\gamma$ denotes surface tension (N/m), $\theta$ denotes a contact angle, $\rho$ denotes density of liquid (kg/m$^3$), g denotes acceleration of gravity (m/s$^2$), and r denotes an inside diameter of the capillary (radius, m). Where the glass capillary is combined with water at a sea level altitude, $\gamma=0.07275$N/m (20° C.), $\theta=20°$, $\rho=1000$ kg/m$^3$, and g=9.80666 m/s$^2$.

From the above, the elevation height h of water in the cylindrical hole 18 is "h=14/capillary radius". When the radius of the capillary diameter of the cylindrical holes 18 is 0.1 mm, the elevation height is 140 mm, which is a sufficiently greater value than the thickness (3 mm) of the capillary pump unit 12, such that a function as the above-described transfer portion is sufficiently achieved.

Next, the number of the cylindrical holes 18 will be discussed. Where cylindrical holes 18 having a diameter (radius) r are arranged in a square lattice shape at an interval d in a region of the suction flow channel 19 having an area S, the number N of the cylindrical holes 18 that can be disposed becomes "$N=S/d^2$". Also, in this case, when the height of the cylindrical holes 18 (a plate thickness of the capillary pump unit 12) is t, the volume V of liquid that can be accommodated in the plurality of cylindrical holes 18 is "$V=N\times\pi\times r^2\times t=S\times\pi\times(r/d)^2\times t$".

As seen from the above equation, even when the diameters (capillary diameters) of the cylindrical holes 18 differ, the same relationship (r/d) with the arrangement interval allows the same liquid volume to be accommodated. However, when the cylindrical hole 18 has a great diameter, the number of the cylindrical holes 18 that can be disposed is reduced, a suction amount per one cylindrical hole 18 is increased, and a distance by which the liquid flows along the suction flow channel 19 to reach the other cylindrical holes 18 is increased. Accordingly, as time lapses, a suction speed is greatly changed and pulsating flow is conspicuous. Thus, cylindrical holes 18 having a smaller diameter in an allowed range may be disposed at smaller intervals in order to suppress pulsating movement in the flow of the sample liquid in the measurement flow channel 15.

Figure 5A:
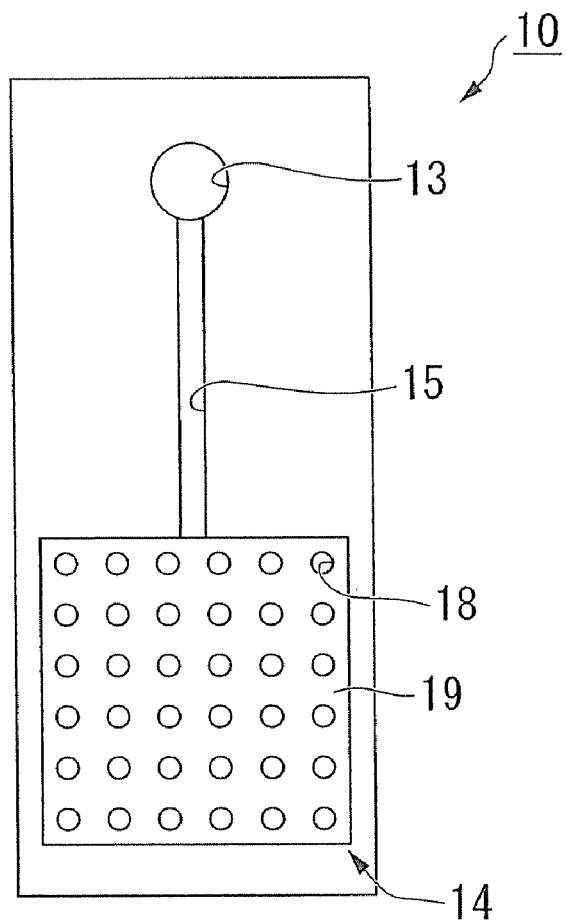
FIG. 5A is a plan view showing an example of a configuration of the flow cell according to the first embodiment.
Figure 5B:
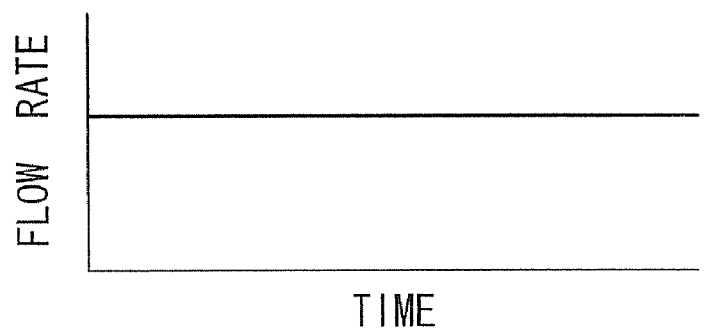
FIG. 5B is a characteristic diagram showing a state of a flow rate according to the first embodiment.

Also, the area of the suction flow channel 19 and the diameter and the number of the cylindrical holes 18 can be properly set to control the flow of the sample liquid in the measurement flow channel 15. For example, as shown in a plan view of FIG. 5A, since a length of the suction flow channel 19 in a width direction (a horizontal direction of FIG. 5A) is made constant and the same number, in the width direction, of cylindrical holes 18 are arranged in a flow channel direction (a vertical direction of FIG. 5A), a constant flow rate is obtained for a predetermined time as shown in a graph of FIG. 5B. For example, the flow rate of the sample liquid in the measurement flow channel 15 can be made constant between a time when the sample liquid flowing through the measurement flow channel 15 reaches the suction flow channel 19 and a time when all the cylindrical holes 18 in the suction flow channel 19 are filled with the sample liquid.

Figure 6A:
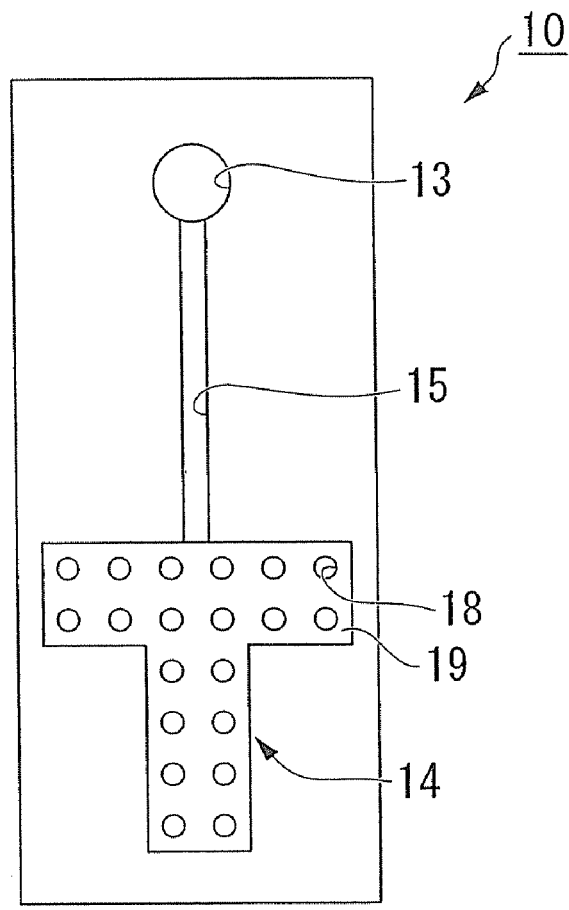
FIG. 6A is a plan view showing an example of a configuration of the flow cell according to the first embodiment.
Figure 6B:
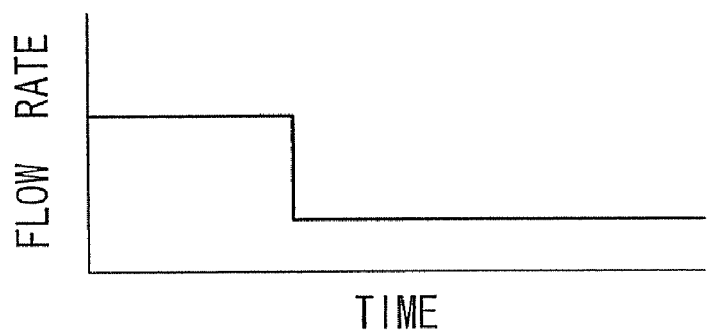
FIG. 6B is a characteristic diagram showing a state of a flow rate according to the first embodiment.

Further, as shown in a plan view of FIG. 6A, a length of the suction flow channel 19 in the width direction may be formed so that a length of a portion apart from the measurement flow channel 15 is smaller than the width of a portion adjacent to the measurement flow channel 15. In this example, the suction flow channel 19 apart from the measurement flow channel 15 has a ½ width. By doing so, as shown in a graph of FIG. 6B, the flow rate decreases after a predetermined time lapses. For example, when a certain time lapses after the sample liquid flowing through the measurement flow channel 15 reaches the suction flow channel 19, the flow rate of the sample liquid in the measurement flow channel 15 can be decreased.

A case where the suction flow channel 19 has a different width from the measurement flow channel 15 will also be described with reference to FIG. 6A. Specifically, a case in which the suction flow channel 19 has a greater width than the measurement flow channel 15 will be described. However, the present invention is not limited to such a configuration. For example, the present invention may have a different configuration, such as a case in which the width of the suction flow channel 19 is smaller than that of the measurement flow channel 15.

Also, the present invention may have a different configuration, such as an example of FIG. 6A in which the length of the suction flow channel 19 in the width direction is formed so that a length of a portion of the suction flow channel 19 apart from the measurement flow channel 15 is greater than the width of a portion of the suction flow channel 19 adjacent to the measurement flow channel 15.

Also, a flow cell 10 having the plurality of sheet-shaped bases 24b sandwiched between the spacer portion 22 and the sheet-shaped base 24a will be described with reference to FIG. 2 of the above-described first embodiment. Although in the first embodiment, a surface of the flat-plate-shaped sheet-shaped base 24b at a side of the sheet-shaped base 24a is referred to as an upper surface and a surface of the sheet-shaped base 24b at a side of the spacer portion 22 is referred to as a lower surface, the present invention is not limited thereto. The surface of the sheet-shaped base 24b in a flat-plate shape at the side of the sheet-shaped base 24a may be referred to as a lower surface and the surface of the sheet-shaped base 24b at the side of the spacer portion 22 may be referred to as an upper surface.

Also, a case where a capillary pump including through holes 27, each making a first point of the sheet-shaped base 24b (in FIG. 2, one point on a surface of the sheet-shaped base 24b in an approximately flat-plate shape at the side of the spacer portion 22 and a second point (in FIG. 2, the other point on a surface of the sheet-shaped base 24b at a side of the sheet-shaped base 24a) communicable with each other, is formed in the sheet-shaped bases 24b will be described with reference to FIG. 2 of the first embodiment described above. However, the present invention is not limited thereto. For example, a capillary pump including through holes, each making one point on the surface of the sheet-shaped base 24b in an approximately flat-plate shape at the side of the spacer portion 22 and the other point on the side of the sheet-shaped base 24b communicable with each other, may be formed in the sheet-shaped base 24b. Alternatively, a capillary pump including through holes, each making one point on the surface of the sheet-shaped base 24b in an approximately flat-plate shape at a side of the spacer portion 22 and the other point on the surface of the sheet-shaped base 24b at a side of the spacer portion 22 communicable with each other, may be formed in the sheet-shaped base 24b.

Figure 7:
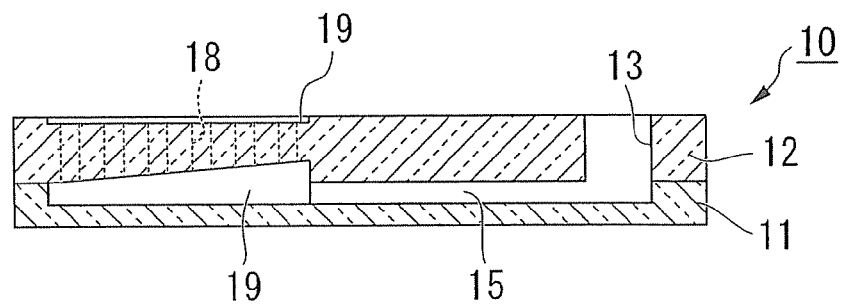
FIG. 7 is a cross-sectional view showing an example of a configuration of the flow cell according to the first embodiment.

Further, an interval of the suction flow channel 19 in a direction opposing the substrate 11 and the capillary pump unit 12, i.e., a height of the suction flow channel 19, increases as the suction flow channel 19 is closer to the measurement flow channel 15, as shown in a cross-sectional view of FIG. 7. Thus, even when the interval varies with a distance from the measurement flow channel 15, the flow rate is changed after a predetermined time lapses.

Next, a second embodiment of the present invention will be described with reference to the accompanying drawings.

Figure 8:
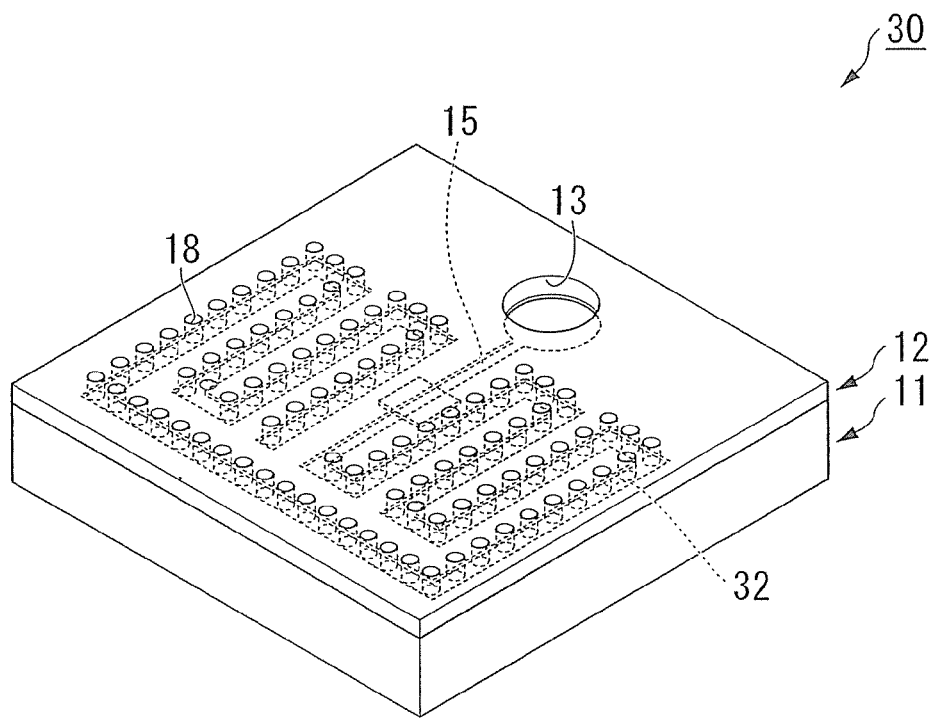
FIG. 8 is a perspective view of a flow cell according to a second embodiment of the present invention.
Figure 9:
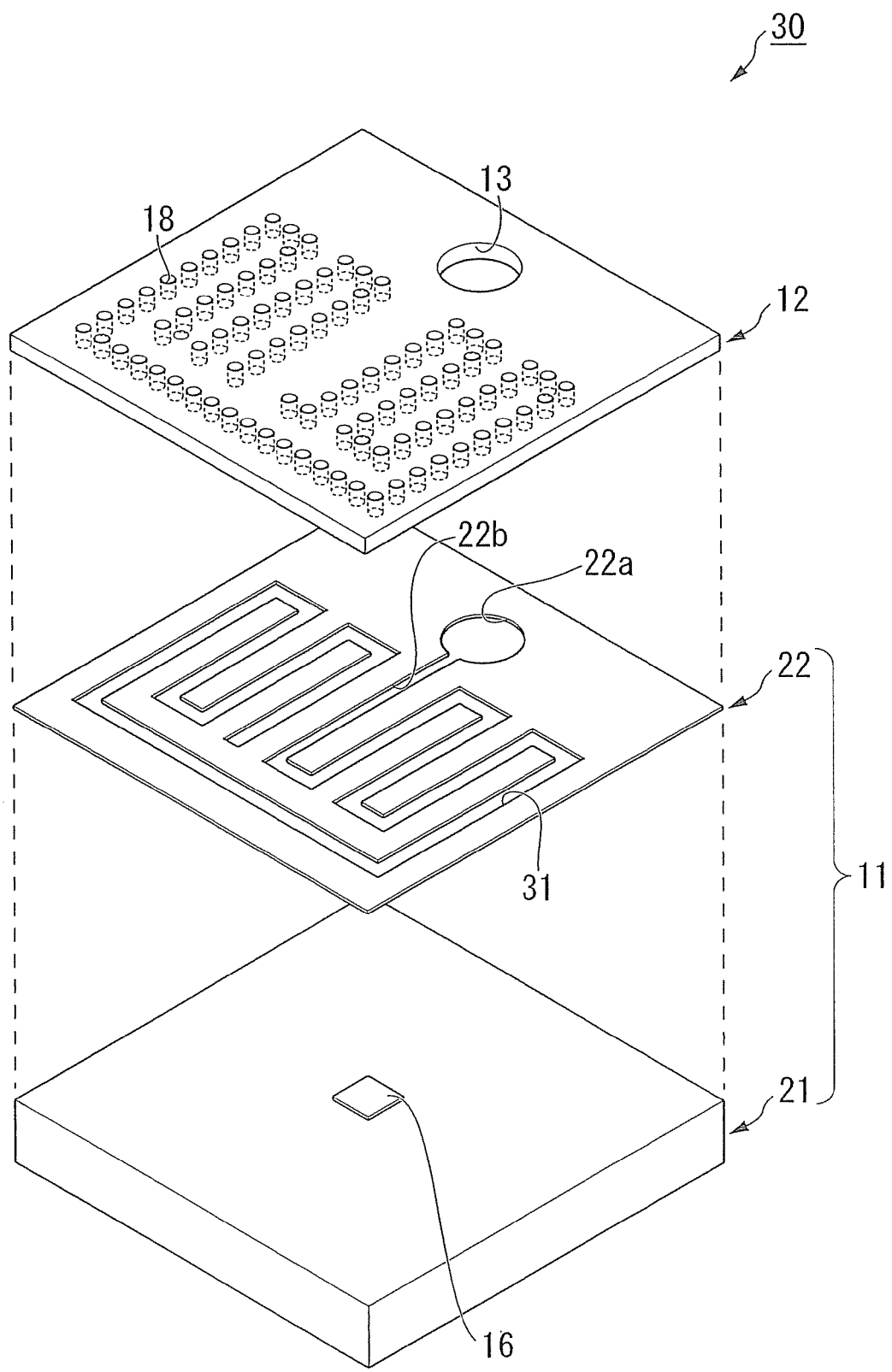
FIG. 9 is an exploded perspective view of the flow cell according to the second embodiment.
Figure 10:
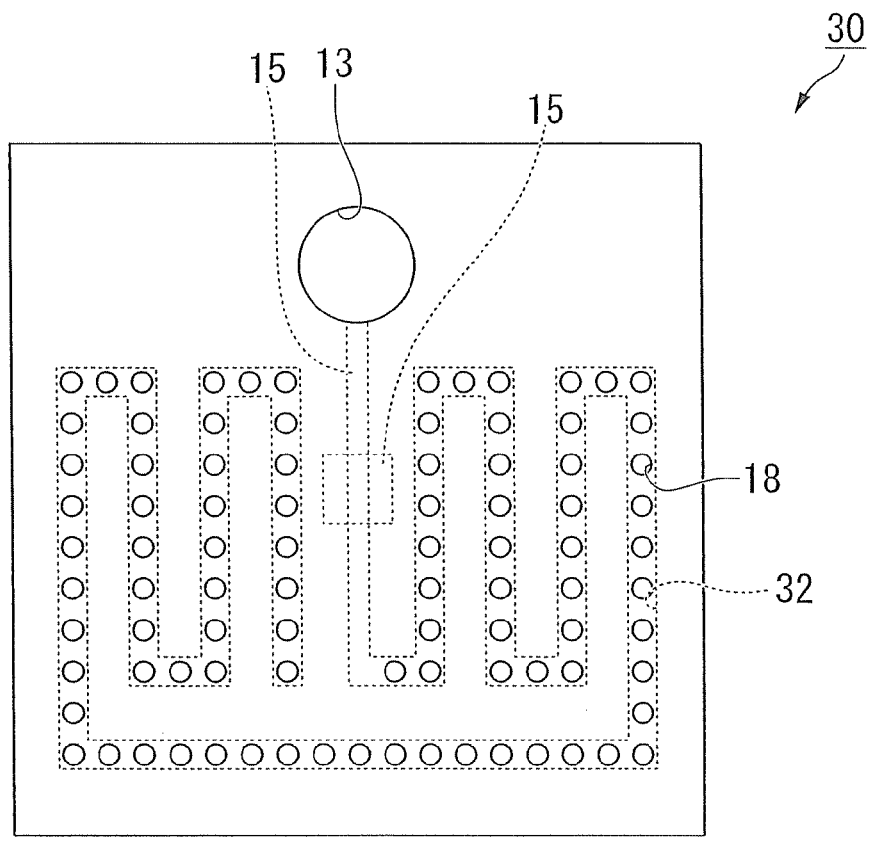
FIG. 10 is a plan view of the flow cell according to the second embodiment.

FIG. 8 is a perspective view of a flow cell according to the second embodiment, FIG. 9 is an exploded perspective view of the flow cell according to the second embodiment, and FIG. 10 is a plan view of the flow cell according to the second embodiment. Also, in FIGS. 8 and 9, like numbers are used to refer to the same components as those of the flow cell 10 of the first embodiment and a detailed description thereof will be omitted.

A flow cell 30 of the present embodiment differs from the flow cell 10 of the first embodiment in formation regions of the suction flow channel 19 and the cylindrical holes 18.

That is, as shown in FIG. 9, the same flow channel groove 22b as in the first embodiment is formed in a spacer portion 22 of a substrate 11 in the present embodiment and a meandering groove 31 extending from a second end of the flow channel groove 22b is formed. The meandering groove 31 is formed with the same width as the flow channel groove 22b, and meanders in regions at both sides of the flow channel groove 22b and extends to surround the both sides of the flow channel groove 22b.

Also, cylindrical holes 18 are formed in a capillary pump unit 12 to correspond to a formation region for the meandering groove 31 in the substrate 11, and more specifically, one cylindrical hole 18 is disposed in a width direction of the meandering groove 31.

As shown in FIGS. 8 and 10, a suction flow channel 32 meandering and extending from a second end of the measurement flow channel 15 by the meandering groove 31 is formed in the flow cell 30 formed by disposing the capillary pump unit 12 on the substrate 11, and a plurality of cylindrical holes 18, one in a width direction, are provided on the suction flow channel 32 in an extending direction of the suction flow channel 32.

Also, in the second embodiment, the capillary pump unit 12 may be formed by stacking a plurality of sheet-shaped bases 24 as in the first embodiment, or by performing a laser processing, and so on, on a single plate-shaped member to form the cylindrical holes 18.

Even in the flow cell 30 of the second embodiment, the sample liquid introduced via the inlet 13 flows through the measurement flow channel 15 due to a capillary force and flows into the suction flow channel 32, as in the flow cell 10 of the first embodiment. The sample liquid reaching the suction flow channel 32 is suctioned up into the cylindrical holes 18 due to the capillary force. Accordingly, the sample liquid is transferred into the measurement flow channel 15 at a predetermined flow rate, and measurement is performed by the detector 16.

According to the flow cell 30, since one cylindrical hole 18 is disposed in the width direction of the suction flow channel 32 and the cylindrical holes 18 are arranged into a line in the extending direction of the suction flow channel 32 as described above, the sample liquid is in turn suctioned into the cylindrical holes 18.

Figure 11:
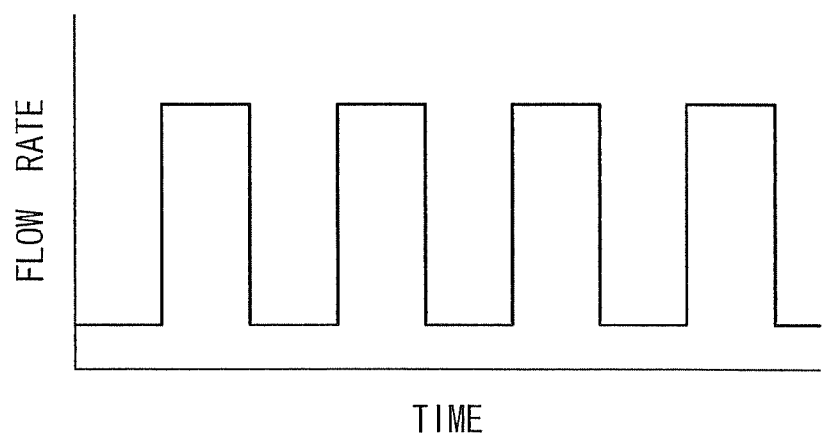
FIG. 11 is a characteristic diagram showing a state of a flow rate of the flow cell according to the second embodiment.

Accordingly, there is a great difference in suction capillary force between locations where the cylindrical hole 18 is formed and locations where the cylindrical hole 18 is not formed, in the suction path of the suction flow channel 32. As a result, the flow rate of the sample liquid flowing through the measurement flow channel 15 can be periodically changed, as shown in FIG. 11.

Further, the flow rate changes with flow channel resistance (a sectional area of the flow channel) in the measurement flow channel 15. As the flow channel resistance increases (the sectional area of the flow channel decreases), periodic elevation of the flow rate due to presence of the cylindrical holes 18 is reduced. Accordingly, where the flow channel resistance exceeds a certain value, the periodic change of the flow rate disappears and the flow rate is substantially constant.

This is because the sample liquid reaches the second cylindrical hole 18 before suction by capillary force in the first cylindrical hole 18 in which the flow channel resistance is high is completed, a state in which the suction by the first cylindrical hole 18 and the suction by the second cylindrical hole 18 are simultaneously performed occurs, and this state simultaneously occurs in the plurality of continuously arranged cylindrical holes 18.

Also, in this state, as the plurality of cylindrical holes 18 are included, the suction operation continues to occur until the sample liquid reaches a rear end of the suction flow channel 32, thus obtaining capability of transferring a sufficient amount of sample liquid.

Figure 12:
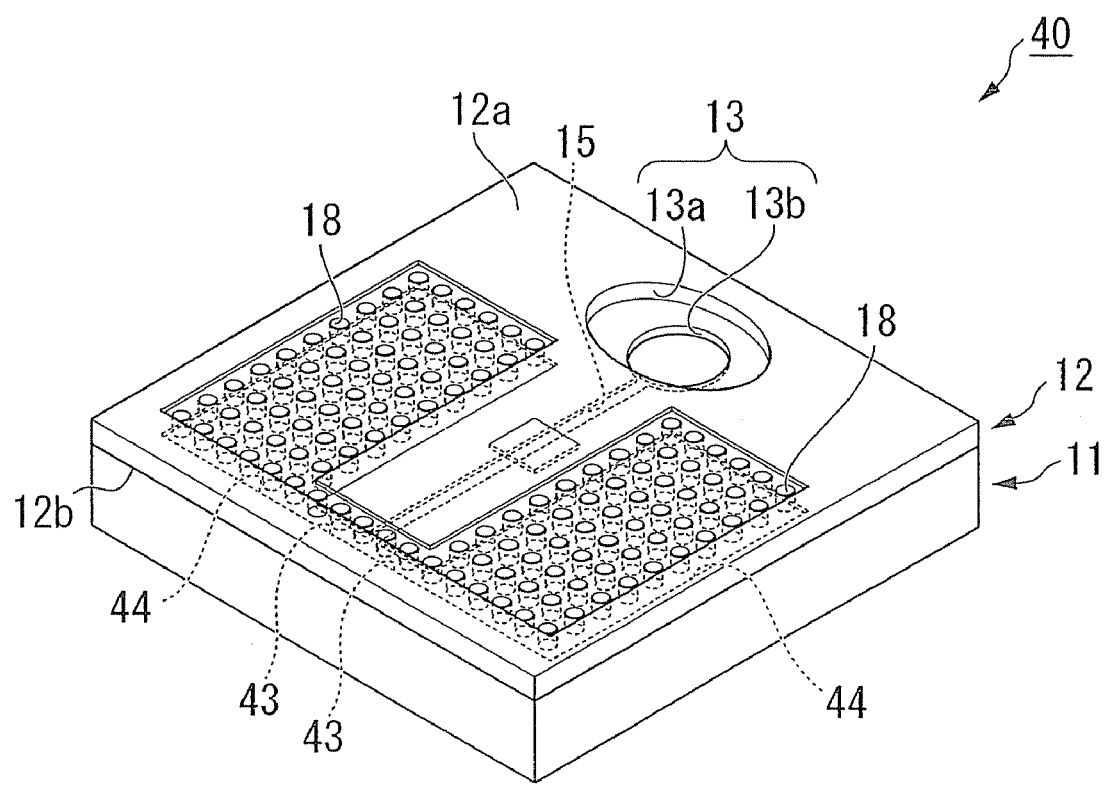
FIG. 12 is a perspective view of a flow cell according to a third embodiment of the present invention.

Next, a third embodiment of the present invention will be described. FIG. 12 is a perspective view of a flow cell according to the third embodiment, FIG. 13 is an exploded perspective view of the flow cell according to the third embodiment, and FIG. 14 is a plan view of the flow cell according to the third embodiment.

Figure 13:
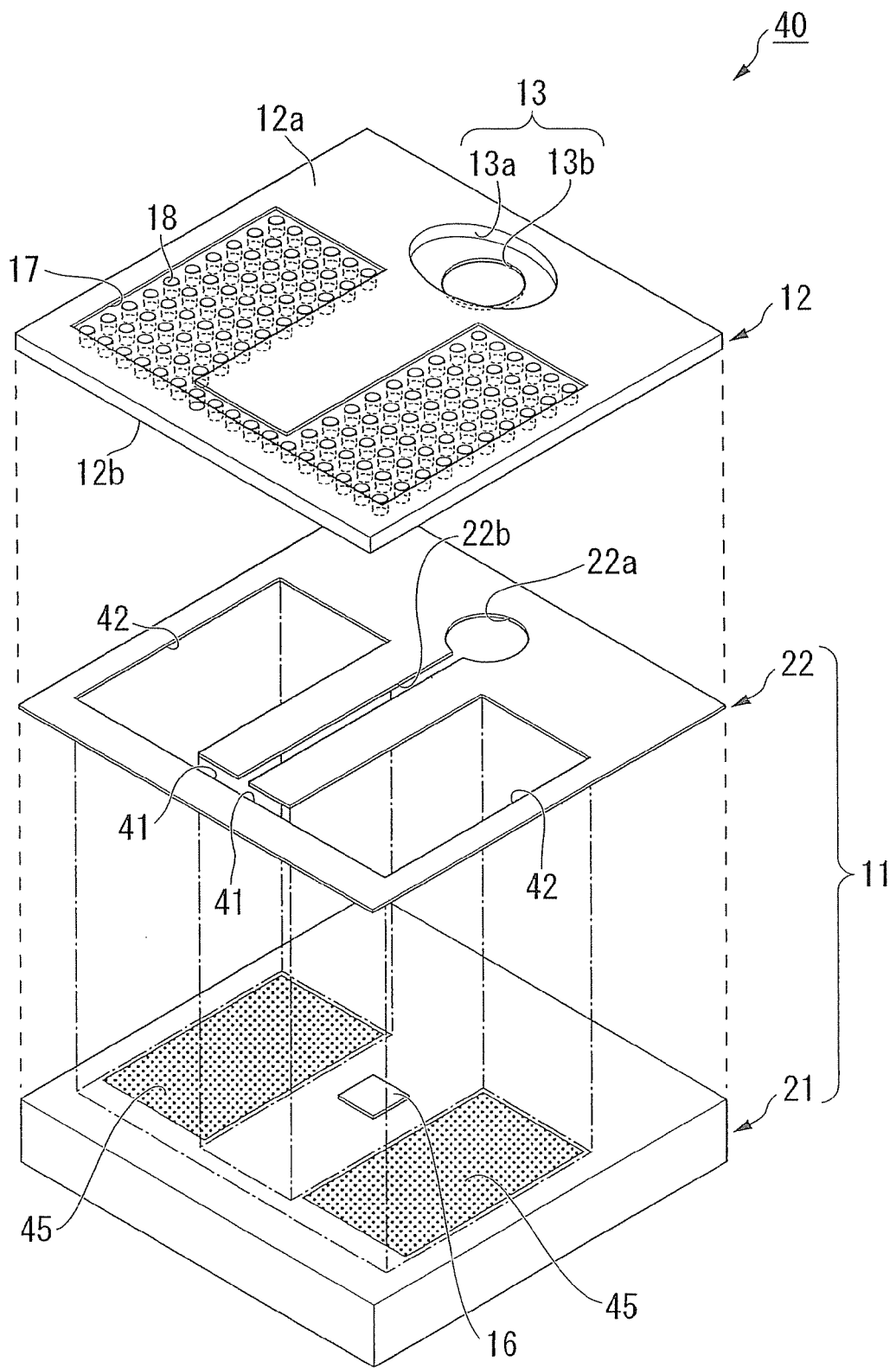
FIG. 13 is an exploded perspective view of the flow cell according to the third embodiment.
Figure 14:
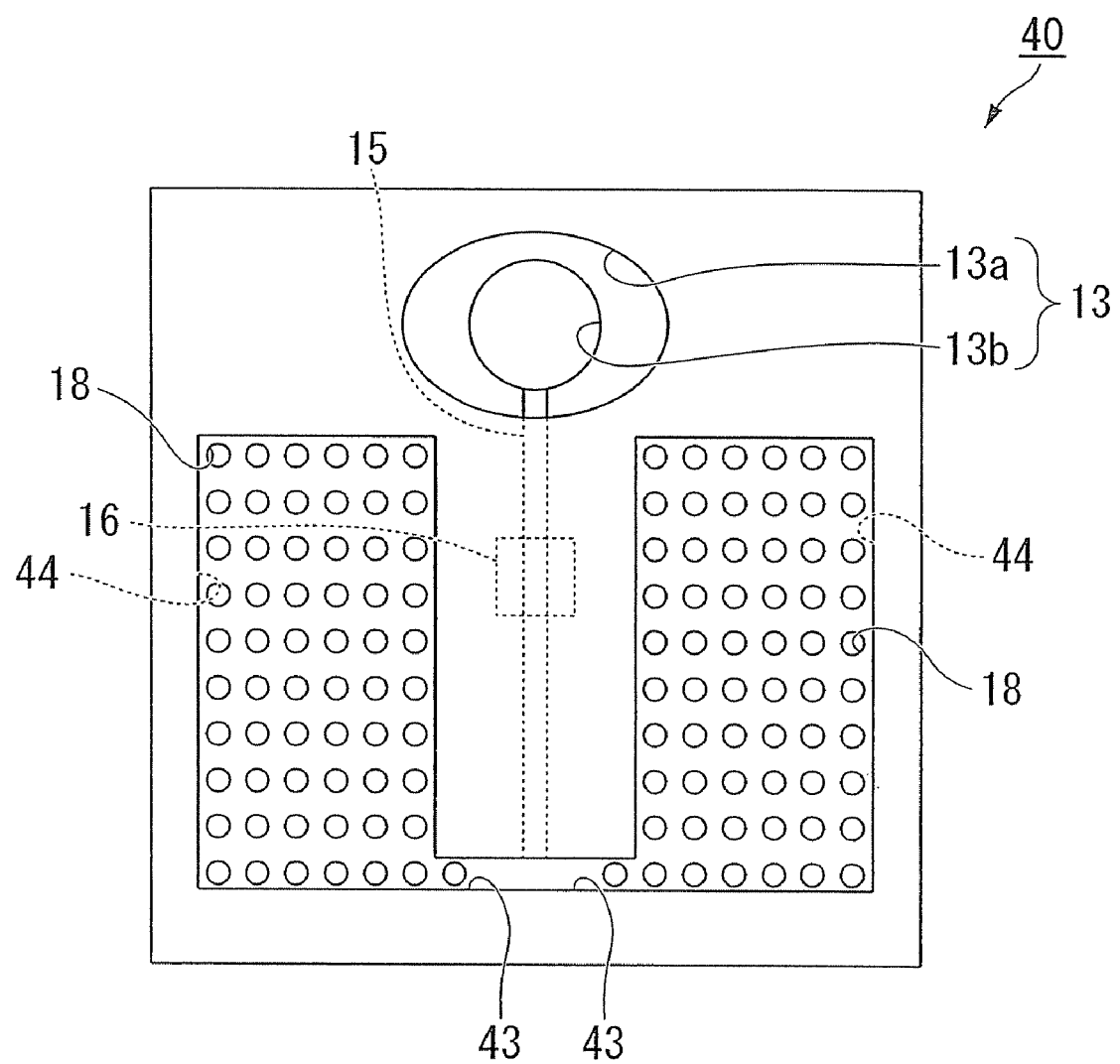
FIG. 14 is a plan view of the flow cell according to the third embodiment.

Also, in FIGS. 12 to 14, like numbers are used to refer to the same components as those of the flow cell 10 of the first embodiment and a detailed description thereof will be omitted.

A flow cell 40 of the present embodiment differs from the flow cell 10 of the first embodiment in formation regions of a suction flow channel 44 and a cylindrical hole 18 and a configuration of an inlet 13. Also, a capillary pump unit 12 may be formed by stacking a plurality of sheet-shaped bases 24, as in the first embodiment, or by performing a laser processing, and so on, on a single plate-shaped member to form cylindrical holes 18.

That is, as shown in FIG. 13, the same flow channel groove 22b as in the first embodiment is formed in a spacer portion 22 of a substrate 11 in the present embodiment, and two branch grooves 41 formed from a second end of the flow channel groove 22b to both sides and rectangular holes 42 respectively connected to the branch grooves 41 are formed.

Further, cylindrical holes 18 are formed in the capillary pump unit 12 to correspond to the branch grooves 41 and the rectangular holes 42 in the substrate 11. More specifically, the cylindrical holes 18 are formed at locations corresponding to the branch grooves 41 so that one cylindrical hole is disposed in a width direction of the branch groove 41. Also, the cylindrical holes 18 are formed at locations corresponding to the rectangular holes 42 to be two-dimensionally disposed on the rectangular holes 42. At the locations corresponding to the branch grooves 41, two or more cylindrical holes 18 may also be disposed in a width direction of the branch groove 41.

And, as shown in FIGS. 12 and 14, two branch flow channels 43 formed from the measurement flow channel 15 by the branch grooves 41 are formed in the flow cell 40 formed by disposing the capillary pump unit 12 on the substrate 11, and a plurality of cylindrical holes 18, one in a width direction of the branch groove 41, are provided on the branch groove 41 in the extending direction of the branch flow channel 43.

Also, suction flow channels 44 connected to the branch grooves 41 and disposed at both sides of the measurement flow channel 15 are provided by the rectangular holes 42. The cylindrical holes 18 of the capillary pump 14 are two-dimensionally disposed on the suction flow channels 44.

Further, in the flow cell 40 of the present embodiment, an inlet 13 includes an inlet (first portion) 13a formed at a side of an upper surface 12a of the capillary pump unit 12, and a communication portion (second portion) 13b formed at a side of a lower surface 12b of the capillary pump unit 12.

The inlet 13a is formed more widely than the communication portion 13b and the inlet 13 is formed in a step shape from the inlet 13a to the communication portion 13b. Accordingly, where the inlet 13 is viewed from above, an upper surface of the step portion including the inlet 13a and the communication portion 13b, as well as a bottom surface of the communication portion 13b, is visible in the inlet 13.

Even in the flow cell 40 of the third embodiment, a sample liquid introduced via the inlet 13 flows through the measurement flow channel 15 due to a capillary force and flows into the branch flow channel 43 and the suction flow channel 44, as in the flow cell 10 of the first embodiment. The sample liquid reaching the branch flow channel 43 and the suction flow channel 44 is suctioned up into the through holes 27 due to the capillary force. Accordingly, the sample liquid is transferred to the measurement flow channel 15 at a predetermined flow rate, and measurement by the detector 16 is performed.

According to the flow cell 40, since the suction flow channel 44 is developed and disposed at sides (both sides) of the measurement flow channel 15, a region of the suction flow channel 44 can increase in size without increasing the entire area of the flow cell 40. Accordingly, the flow cell 40 can be made compact and the capacity of the capillary pump 14 can be increased.

Further, the inlet 13 including the inlet 13a and the communication portion 13b makes it more easy to visibly confirm a reduction amount of the sample liquid introduced to the inlet 13. For example, if a volume of the inlet 13a is known, consumption of the sample liquid having a known volume can be checked at a time when exposure of the upper surface of the step portion is visibly confirmed after the sample liquid is introduced.

Also, in the flow cell 40 of the third embodiment, for example, a surface active region 45 having a different wettability for a sample liquid than other regions may be formed on a surface of the base substrate 21 in a formation region for the suction flow channel 44, as shown in FIG. 13. Since an expanding state of the sample liquid in the surface active region 45 differs from that of other regions, a suction state of the sample liquid in the suction flow channel 44 can controlled and the flow rate of the sample liquid flowing the measurement flow channel 15 can be changed by changing an area of the surface active region 45. Also, the formation region for the surface active region 45 is not limited to the formation region for the suction flow channel 44, but may be provided in the formation region for the measurement flow channel 15.

The surface active region 45 can be formed by performing surface processing, for example, with BlockAce (registered trademark of Dainippon Sumitomo Pharma Co. Ltd.). For example, where the base substrate 21 is formed of glass, the flow rate of the sample liquid (phosphate buffer solution) in the measurement flow channel 15 of the flow cell 40 in which the surface active region 45 is not formed is 17.1 μl/min while the flow rate of the sample liquid in the measurement flow channel 15 of the flow cell in which the surface active region 45 is formed increases to 50.0 μl/min.

Also, where the base substrate 21 is formed of transparent plastic, the flow rate of the sample liquid in the measurement flow channel 15 of the flow cell in which the surface active region 45 is not formed is 1.4 μl/min while the flow rate of the sample liquid in the measurement flow channel 15 of the flow cell in which the surface active region 45 is formed increases to 37.5 μl/min. Thus, for plastic having low wettability, the flow rate is greatly changed depending on the presence or absence of the surface active region 45.

Also, where the thin metallic film is formed as the detector 16 in the entire area of the substrate 11, the surface active region 45 is formed on the thin metallic film. In this case, when the surface active region 45 is not formed, the flow rate of the sample liquid in the measurement flow channel 15 is 2.0 μl/min while the flow rate of the sample liquid in the measurement flow channel 15 of the flow cell 40 in which the surface active region 45 is formed increases to 15.0 μl/min.

Here, in the first, second and third embodiments described above, a color change portion, the color of which is changed when brought into contact with the sample liquid, may be included in the outlet portion 17 through which the sample liquid is leaked from the cylindrical holes 18. An example of the color change portion includes a color change layer formed of magnesium perchlorate or cobalt chloride.

Where the color change layer (color change portion) formed of the magnesium perchlorate is included, the portion is changed from yellow to blue when brought into contact with the sample liquid, including water. Also, where the color change layer is formed of the cobalt chloride, the portion is changed from blue to red when brought into contact with the sample liquid, including water.

Accordingly, a reach state of the sample liquid in the suction flow channels 19, 32 and 44 can be confirmed visibly. As a result, the speed or total amount of transferred liquid, for example, can be recognized visibly.

Next, a fourth embodiment of the present invention will be described in detail with reference to FIGS. 15 to 17.

Figure 15:
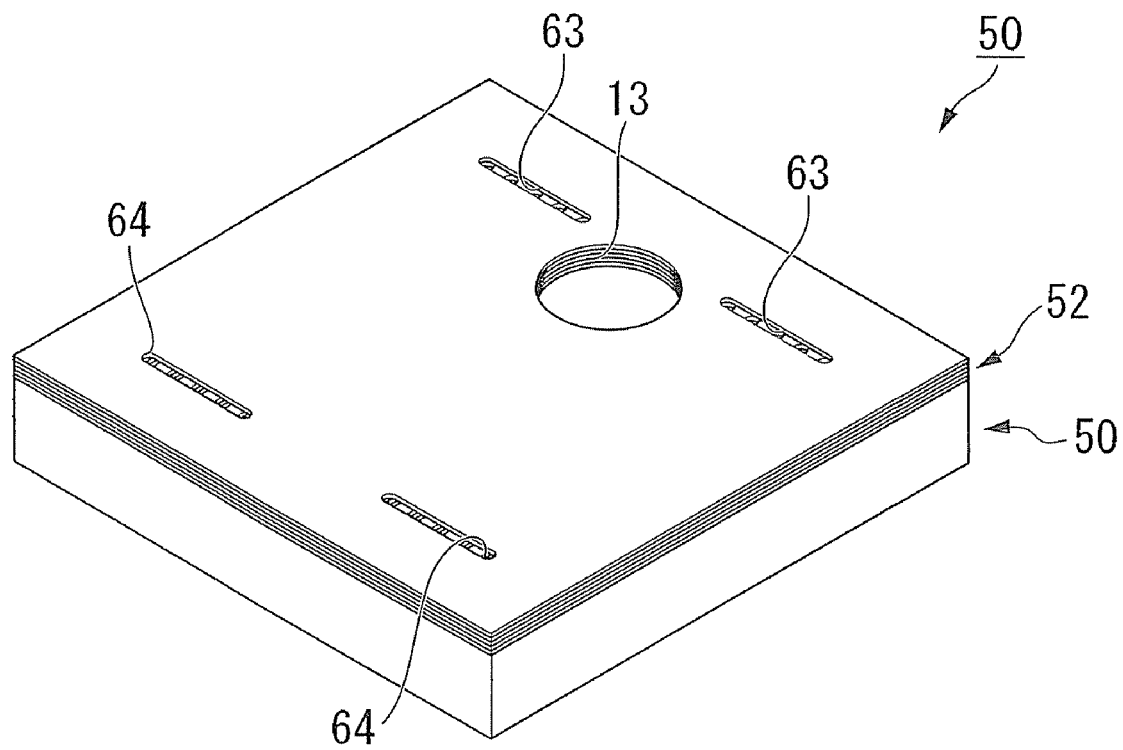
FIG. 15 is a perspective view of a flow cell according to a fourth embodiment of the present invention.
Figure 16:
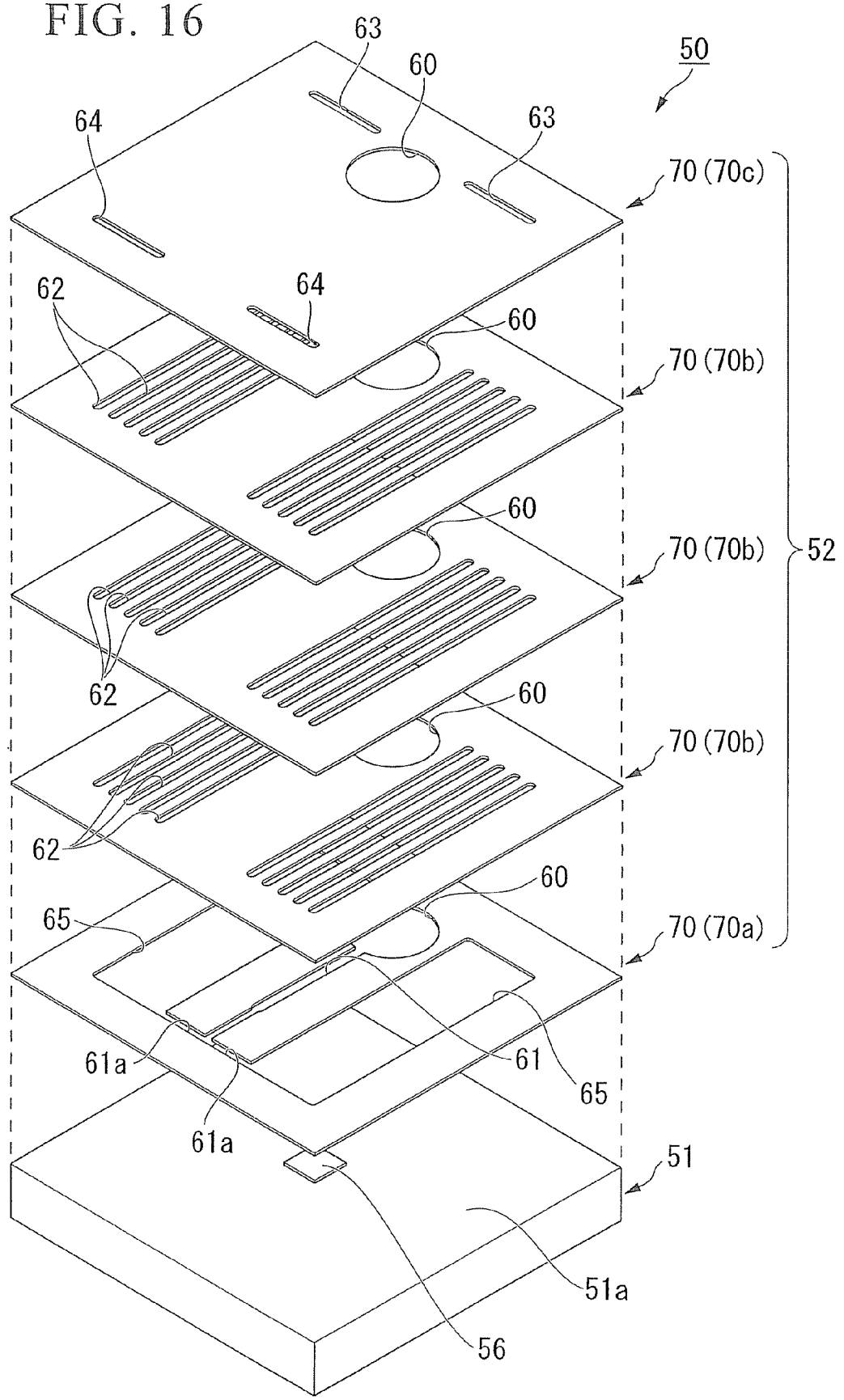
FIG. 16 is an exploded perspective view of the flow cell according to the fourth embodiment.
Figure 17:
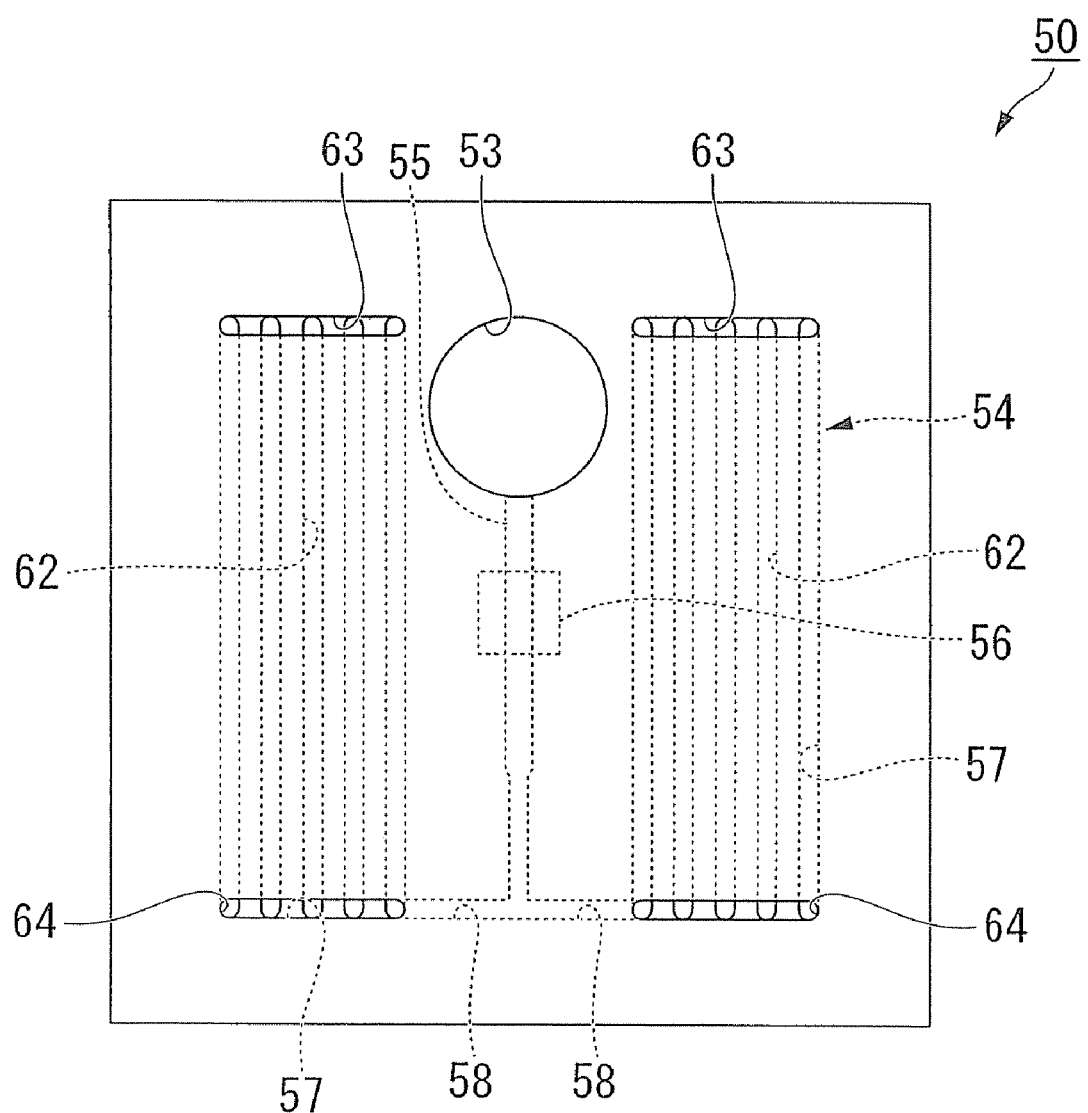
FIG. 17 is a plan view of the flow cell according to the fourth embodiment.

FIG. 15 is a perspective view of a flow cell of the fourth embodiment, FIG. 16 is an exploded perspective view of the flow cell of the fourth embodiment, and FIG. 17 is a plan view of the flow cell of the fourth embodiment.

As shown in FIG. 15, a flow cell 50 of the present embodiment is formed by stacking a capillary pump unit 52 having the same outside dimension as a substrate 51 that is in an approximately rectangular plate shape when viewed from above, on the substrate 51.

Also, the capillary pump unit 52 is formed by stacking a plurality of sheet-shaped bases 70, as shown in FIG. 16.

Specifically, the flow cell 50 includes an inlet 53 through which sample liquid is introduced, a capillary pump 54, a suction flow channel 57 disposed below the capillary pump 54, a measurement flow channel 55 and coupling flow channels 58 that connect between the suction flow channels 57 and the inlet 53, and a detector 56 disposed on the measurement flow channel 55, as shown in FIG. 17.

Also, although a plurality of through grooves 62 of sheet-shaped bases 70b are contained in a rectangular region where the rectangular grooves 65 of a sheet-shaped base 70a are formed as illustrated in FIG. 16, the present invention is not limited thereto. If the through grooves 62 of the sheet-shaped bases 70b disposed at the top and bottom and the through grooves 62 of the sheet-shaped base 70b between the sheet-shaped bases 70b disposed at the top and bottom are spatially connected to one another, the through grooves 62 of the sheet-shaped bases 70b may have any other shape.

The substrate 51 is formed of, for example, optical glass, such as BK7, or a polymer material, and is in an approximately rectangular shape, when viewed from above, having a plate thickness of about 1 mm and each sides thereof being about 16 mm. Also, the detector 56 formed as a thin metallic film is provided on an upper surface 51a of the substrate 51. Examples of a material of the thin metallic film include Au, and so on, and the thin metallic film is formed by deposition, sputtering, plating processing, or the like on the upper surface 51a of the substrate 51.

The detector 56 may also be formed in only a portion corresponding to the measurement flow channel 55.

The sheet-shaped base 70 is in a rectangular shape, when viewed from above, having the same peripheral size as the substrate 11, as shown in FIG. 16. The sheet-shaped base 70 is formed as a thin film having a thickness of 10 μm to 100 μm. Also, in the present embodiment, the sheet-shaped base 70 is formed in a double-sided tape form in which both sides are coated with adhesive. For example, TL-400S series available from Lintec Corporation, general-purpose double-sided tape 9313 available from Sumitomo 3M Limited, ARcare series available from NIPPN TechnoCluster, Inc., or the like is used. Alternatively, the sheet-shaped base 70 may be in a single sided tape shape in which a first side is coated with adhesive, rather than in the double-sided tape shape in which both sides of the sheet-shaped base 70 are coated with adhesive.

Also, the sheet-shaped base 70 is not limited to the double-sided tape shape, and may be formed of acryl or glass in a thin film form, or of a metallic sheet, ceramic sheet, or the like. Also, the thickness of the sheet-shaped base 70 is not limited to the above range and may range, for example, from 100 μm to several mm.

Further, in each sheet-shaped base 70, a circular hole 60 is formed in a region beside a first side in a longitudinal direction and in a region of an approximately central portion of the side in a width direction (a direction parallel to the side). When the sheet-shaped bases 70 are stacked, the respective circular holes 60 overlap one another to form the above-described inlet 53.

Further, a flow channel groove 61 having a first end connected to the circular hole 60 and extending in a straight line shape toward an opposite side is formed in the sheet-shaped base 70a that is the bottom layer contiguous to the substrate 51 among the plurality of sheet-shaped bases 70. The flow channel groove 61 has a second end connected to coupling flow channel grooves 61a that are orthogonal to the flow channel groove 61 and extend toward both sides of the circular hole 60. In addition, rectangular grooves 65, of which the longitudinal direction is parallel to the flow channel groove 61, are formed at both ends of the coupling flow channel grooves 61a.

Also, although the case where the rectangular grooves 65 are formed in the sheet-shaped base 70a has been described in the present embodiment, the present invention is not limited thereto. For example, grooves having a circular shape, a triangular shape, or the like rather than the rectangular shape, may be formed in the sheet-shaped base 70a.

A plurality of through grooves (through holes) 62 are formed at locations corresponding to the rectangular grooves 65, so that a formation region thereof is located on the rectangular grooves 65, in the sheet-shaped bases 70b, which are a plurality of intermediate layers sequentially stacked on the sheet-shaped base 70a that is the bottom layer. Also, in the present embodiment, the respective through grooves 62 are formed in parallel with the flow channel groove 61.

When the sheet-shaped bases 70b are stacked as the intermediate layers, the respective through grooves 62 are communicable with one another, such that a plurality of slit-shaped hollow portions are formed inside the stacked sheet-shaped bases 70b.

The hollow portions cause a capillary force and function as a capillary pump 54 which suctions the sample liquid.

Further, in the sheet-shaped base 70c that is a top layer, air grooves 63 in a rectangular shape, when viewed from above, are formed in regions at both sides of the circular hole 60 in a width direction and a region beside the a first side in a longitudinal direction, and air grooves 64 in a rectangular shape, when viewed from above, are formed in regions at both sides of the same circular hole 60 and in a region beside an opposite side.

The respective air grooves 63 and 64 are communicable with the through grooves 62 of the sheet-shaped bases 70b that are the intermediate layers.

In the present embodiment, the flow cell 50 is formed by stacking the substrate 51 and the plurality of sheet-shaped bases 70 that are described above.

Specifically, where the plurality of sheet-shaped bases 70 are in a double-sided tape form, the sheet-shaped bases 70 are sequentially disposed on the upper surface of the substrate 51 to be adhered, such that the sheet-shaped bases 70 form the capillary pump unit 52. Accordingly, the substrate 51 and the capillary pump unit 52 are integrally fixed to constitute the flow cell 50.

Also, where the sheet-shaped bases 70 are formed of acryl or glass, or of a metallic sheet, a ceramic sheet or the like, the sheet-shaped bases 70 are integrally stacked using adhesive, a plurality of sheet-shaped bases 70 are sequentially disposed on an upper surface of the capillary pump unit 52 and then heated or irradiated with laser light to be welded, or the sheet-shaped bases 70 are integrally formed using anodic bonding, such that the substrate 51 and the respective sheet-shaped bases 70 are integrally fixed to form the flow cell 50.

In the flow cell 50 in the present embodiment, the flow channel groove 61 formed in the sheet-shaped base 70a that is a bottom layer is regarded as the measurement flow channel 55 on the substrate 51 and a detector 56 is disposed on the measurement flow channel 55. Also, the coupling flow channel groove 61a is regarded as the coupling flow channel 58 and the rectangular grooves 65 are regarded as suction flow channels 57. Also, the respective through grooves 62 of the sheet-shaped bases 70b that are intermediate layers are communicable with one another, and a capillary pump 54 including a plurality of slit-shaped hollow portions is formed.

Further, in the present embodiment, the flow cell 50 may not include the inlet 53, the measurement flow channel 55, and the detector 56, as in the first embodiment. Even in this case, the sample liquid introduced to the suction flow channel 57 via another flow channel (not shown) is transferred upward by the capillary pump 14.

Also, although the case where the five sheet-shaped bases 70 are used has been described in the present embodiment, the present invention is not limited thereto and for example tens or hundreds of sheet-shaped bases 70 may be stacked.

Next, an operation of the flow cell 50 according to the present embodiment will be described.

When a sample liquid is injected into the inlet 53, the sample liquid flows into the measurement flow channel 55 due to a capillary force. When the sample liquid passes through the detector 56 on the measurement flow channel 55, the above-described measurement using a surface plasmon resonance phenomenon is performed.

When the sample liquid passing through the measurement flow channel 55 passes through the coupling flow channels 58 and reaches the suction flow channel 57, the sample liquid flows into the capillary pump 54 to fill it by capillary force of the capillary pump 54 including the through grooves 62. When the sample liquid reaches an upper portion of the capillary pump 54, capillary force does not work in the air grooves 63 and 64 and the sample liquid stops movement. Accordingly, the sample liquid suction operation in the capillary pump 54 is terminated.

Here, in order to successfully perform sample liquid measurement, it is necessary to continuously flow the sample liquid in the measurement flow channel 55, which requires a large capacity of the capillary pump 54 that can accommodate the sample liquid.

In this regard, in the flow cell 50 according to the present embodiment, since the capillary pump 54 is formed by stacking the plurality of sheet-shaped bases 70, the flow cell 50 can be larger in a height direction by increasing the number of the sheet-shaped bases 70 and the capillary pump 54 can be readily formed in a structure of a high aspect ratio.

Accordingly, since a large volume of the capillary pump 54 in a stacking direction can be reserved, the capacity that can accommodate a sample liquid is increased, such that the sample liquid can be continuously flowed by the measurement flow channel 55. Thus, since the sample liquid measurement can be successfully performed, measurement precision can be improved.

Also, since the through grooves 62 formed in the respective stacked sheet-shaped bases 70 are communicable with one another, very small spaces where a capillary force occurs can be formed in all areas of the stacked sheet-shaped bases 70 in a vertical direction, thereby achieving a highly efficient use of space in the flow cell 50.

A flow cell 80 according to a fifth embodiment of the present invention will now be described with reference to FIGS. 18 and 19.

Figure 18:
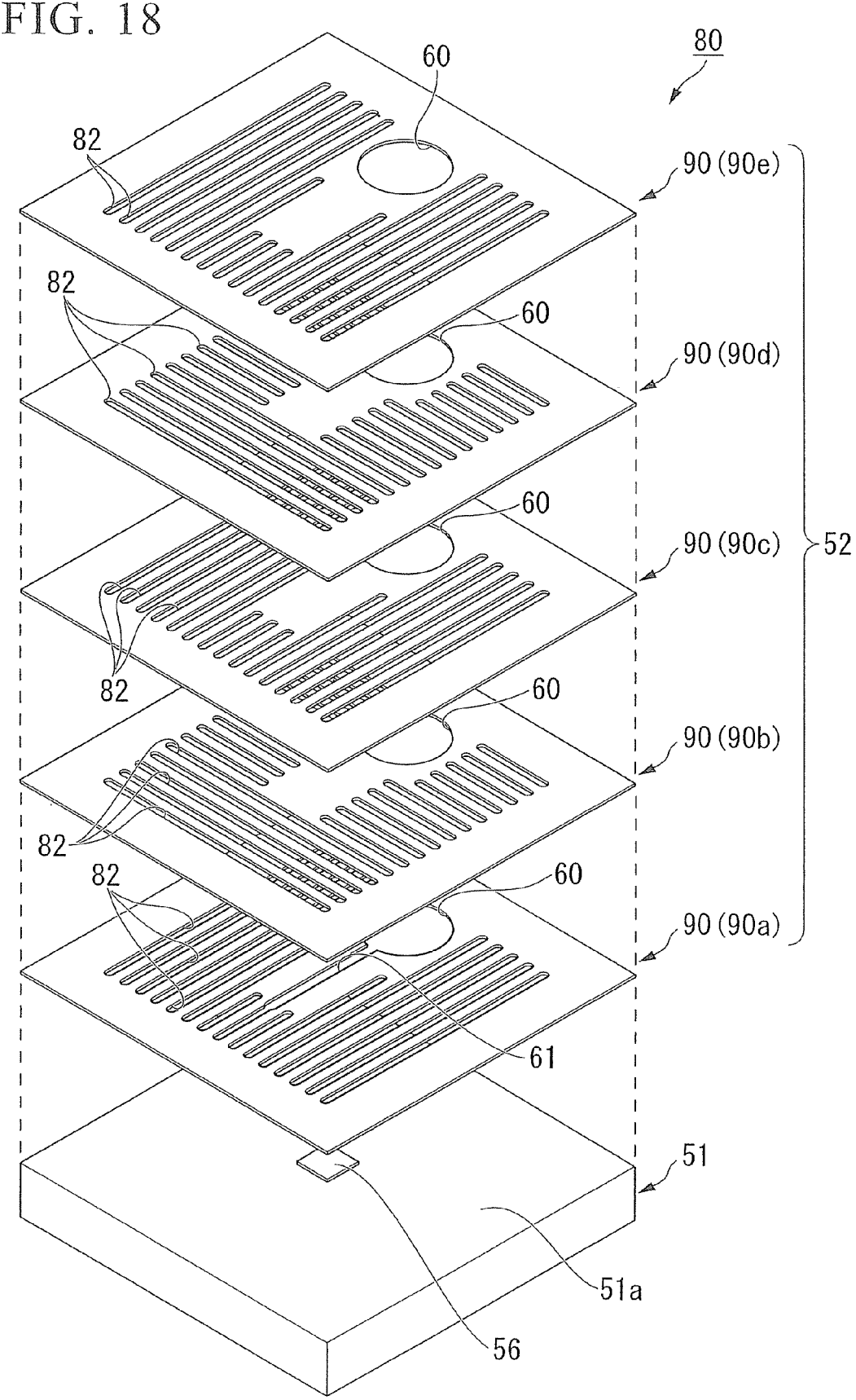
FIG. 18 is an exploded perspective view of the flow cell according to the fifth embodiment.
Figure 19:
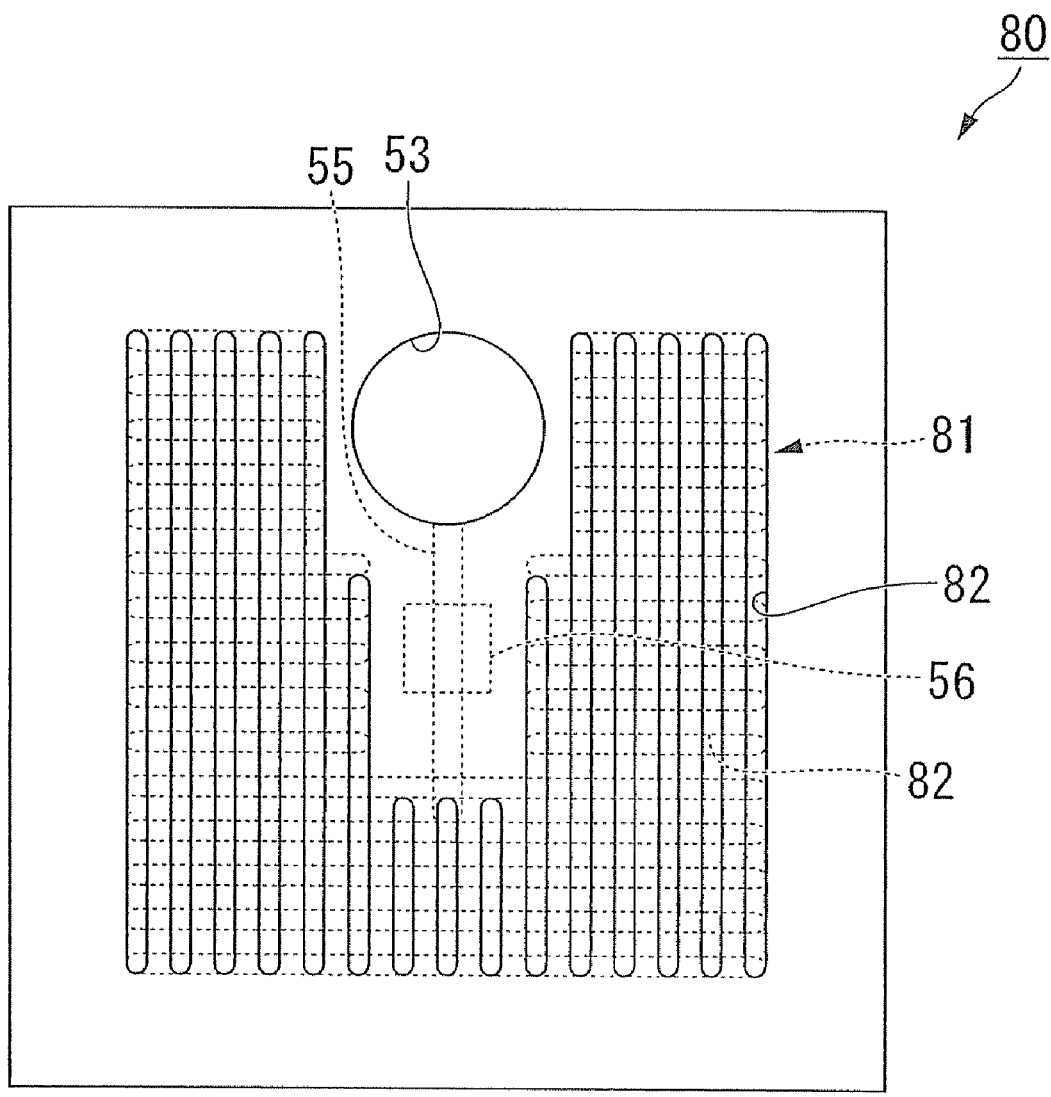
FIG. 19 is a plan view of the flow cell according to the fifth embodiment.

FIG. 18 is an exploded perspective view of a flow cell of a fifth embodiment, and FIG. 19 is a plan view of the fifth embodiment. In FIGS. 18 and 19, like numbers are used to refer to the same components as those of the fourth embodiment and a detailed description thereof will be omitted.

A capillary pump 81 in a flow cell 80 of the fifth embodiment differs from the flow cell 50 of the fourth embodiment in that while the capillary pump 54 in the flow cell 50 includes very small spaces in a slit shape including the through grooves 62 formed in parallel with one another, a capillary pump 81 in the flow cell 80 includes a very small space in a parallel-cross shape.

As shown in FIG. 18, a flow channel groove 61 having a first end connected to a circular hole 60 and extending in a straight line shape from a first side to an opposite side in longitudinal direction (in parallel with a through groove 82) is formed in a sheet-shaped base 90a that is a bottom layer contiguous to a substrate 51 among a plurality of sheet-shaped bases 90 constituting the capillary pump unit 52.

A plurality of through grooves 82 in a straight line shape provided in parallel with the flow channel groove 61 are also formed in the sheet-shaped base 90a that is a bottom layer, a formation region thereof is regarded as an approximately U-shape when viewed from above, and the circular hole 60 is disposed in a U-shaped opening.

Also, a second end of the flow channel groove 61 is connected to a portion of the through groove 82.

Further, a plurality of through grooves 82 are formed even in a plurality of sheet-shaped bases 90b, 90c, 90d and 90e sequentially stacked on the sheet-shaped base 90a that is the bottom layer, so that a formation region thereof is in an approximately U-shape when viewed from above.

Here, the plurality of through grooves 82 in the sheet-shaped base 90b that is the intermediate layer stacked directly on the sheet-shaped base 90a that is the bottom layer are formed to be orthogonal to the plurality of through grooves 82 in the sheet-shaped base 90a that is the bottom layer. Also, the through grooves 82 of the sheet-shaped base 90b are orthogonal to the through grooves 82 of the sheet-shaped base 90c stacked on the sheet-shaped base 90b, the through grooves 82 of the sheet-shaped base 90c are orthogonal to the through grooves 82 of the sheet-shaped base 90d stacked on the sheet-shaped base 90c, and the through grooves 82 of the sheet-shaped base 90d are orthogonal to the through grooves 82 of the sheet-shaped base 90e stacked on the sheet-shaped base 90d.

Thus, the bottom layer in the flow cell 80 of the present embodiment and the sheet-shaped bases 90a, 90b, 90c, 90d and 90e stacked on the bottom layer are formed so that the respective through grooves 82 of the vertically contiguous sheet-shaped bases 90 are orthogonal to each other, for example, so that a direction of the through grooves 82 are changed 90° as the sheet-shaped bases 90 are sequentially stacked.

When the sheet-shaped bases 90a, 90b, 90c, 90d, and 90e are stacked, the respective through grooves 82 are communicable with one another, such that hollow portions are formed in a parallel-cross shape inside the stacked sheet-shaped bases 90. The hollow portions cause a capillary force and function as the capillary pump 81 which suctions the sample liquid.

Also, although the case where the five sheet-shaped bases 90 are used has been described in the present embodiment, the present invention is not limited thereto and more, for example, tens to hundreds, of sheet-shaped bases 90 may be stacked.

The flow cell 80 of the fifth embodiment had the following operation and effects, in addition to the operation and effects of the flow cell 40 of the fourth embodiment.

That is, the respective through grooves 82 of the vertically contiguous sheet-shaped bases 90 are formed to be orthogonal to each other, and the very small spaces in a parallel-cross shape formed of the through grooves 82 communicable with one another are used as the capillary pump 81. Accordingly, a great contact area between the sample liquid and the sheet-shaped bases 90 can be reserved, and high capillary force can be obtained. Accordingly, the sample liquid can be efficiently suctioned and smoothly measured.

Although the flow cells 10, 30, 40, 50, and 80 according to the embodiments of the present invention have been described in detail with reference to the drawings, a detailed configuration is not limited to the embodiments and may be changed without departing from the spirit and scope of the present invention.

For example, although the examples in which the five sheet-shaped bases 70 and 90 are stacked are shown in the fourth and fifth embodiments, the present invention is not limited thereto and a plurality of sheet-shaped bases 70 and 90 may be stacked to constitute the flow cells 50 and 80. For example, where 100 sheet-shaped bases 70 and 90 having a thickness of 10 μm to 100 μm are stacked, the capillary pumps 54 and 81 have a thickness of 1 to 10 mm and very small dense spaces therein.

Further, although the measurement using surface plasmon resonance phenomenon has been particularly described in the embodiments, the present invention is not limited thereto, and other optical measurement methods may be used as long as the methods can handle the sample liquid.

Although the case where the substrates 11 and 51 are formed of transparent optical glass has also been described in the present embodiment, the present invention is not limited thereto and the substrates 11 and 51 may be formed of a material that light does not transmit through.

Industrial Applicability

The present invention can be applied to a capillary pump having a high pump capacity with a high aspect ratio and a highly efficient use of space that can be fabricated with a small size at a low cost, a capillary pump unit, and a flow cell using the capillary pump, and so on.

The invention claimed is:
1. A capillary pump unit comprising:
an approximately flat-plate-shaped base substrate;
an approximately flat-plate-shaped spacer portion formed on the approximately flat-plate-shaped base substrate, the approximately flat-plate-shaped spacer portion comprising a flow channel groove;
an approximately flat-plate-shaped base formed on the approximately flat-plate-shaped spacer portion;
a capillary pump comprising a plurality of through portions making a first point and a second point of the approximately flat-plate-shaped base communicable with each other, the capillary pump being formed in the approximately flat-plate-shaped base; and
an inlet formed in the approximately flat-plate-shaped base,
wherein the inlet distributes sample liquid to the plurality of through portions through the flow channel groove, and
the sample liquid is transferred from the first point to the second point by capillary force by the plurality of through portions,
wherein the base comprises a plurality of stacked sheet-shaped bases, and
the plurality of through portions are formed in the respective sheet-shaped bases so that the through portions are communicable with one another among the sheet-shaped bases, and
wherein the through portions are a plurality of through grooves provided in parallel with one another in the respective sheet-shaped bases, and
the sheet-shaped bases are stacked so that the through grooves of adjacent ones of the sheet-shaped bases overlap in parallel with one another.

2. A capillary pump unit, comprising:
an approximately flat-plate-shaped base substrate;
an approximately flat-plate-shaped spacer portion formed on the approximately flat-plate-shaped base substrate, the approximately flat-plate-shaped spacer portion comprising a flow channel groove;
an approximately flat-plate-shaped base formed on the approximately flat-plate-shaped spacer portion;
a capillary pump comprising a plurality of through portions making a first point and a second point of the approximately flat-plate-shaped base communicable with each other, the capillary pump being formed in the approximately flat-plate-shaped base; and
an inlet formed in the approximately flat-plate-shaped base,
wherein the inlet distributes sample liquid to the plurality of through portions through the flow channel groove, and
the sample liquid is transferred from the first point to the second point by capillary force by the plurality of through portions,
wherein the base comprises a plurality of stacked sheet-shaped bases, and
the plurality of through portions are formed in the respective sheet-shaped bases so that the through portions are communicable with one another among the sheet-shaped bases, and
wherein the through portions are a plurality of through grooves provided in parallel with one another in the respective sheet-shaped bases, and the sheet-shaped bases are stacked so that the through grooves of adjacent ones of the sheet-shaped bases intersect and overlap each other.

3. The capillary pump unit according to claim 1 or 2, wherein the sheet-shaped base is a seal to which both sides or a single side can be adhered, and
the plurality of the seals are adhered to one another and stacked.

4. The capillary pump unit according to claim 1 or 2, wherein the sheet-shaped base is formed of synthetic resin or glass, and
a plurality of synthetic resin or glass are welded to one another and stacked.

5. The capillary pump unit according to claim 1 or 2, wherein the through portions are a plurality of through holes formed in the respective sheet-shaped bases, and
the sheet-shaped bases are stacked so that at least some of the through holes of the adjacent ones of the sheet-shaped bases overlap each other.

* * * * *